(12) United States Patent
Ushigome

(10) Patent No.: US 10,006,885 B2
(45) Date of Patent: Jun. 26, 2018

(54) QCM SENSOR AND METHOD OF MANUFACTURING THE SAME

(71) Applicant: FUJITSU LIMITED, Kawasaki-shi, Kanagawa (JP)

(72) Inventor: Michio Ushigome, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 583 days.

(21) Appl. No.: 14/612,549

(22) Filed: Feb. 3, 2015

(65) Prior Publication Data

US 2015/0168351 A1  Jun. 18, 2015

Related U.S. Application Data

(63) Continuation of application No. PCT/JP2012/070520, filed on Aug. 10, 2012.

(51) Int. Cl.
| | |
|---|---|
| *G01N 29/036* | (2006.01) |
| *G01N 29/22* | (2006.01) |
| *G01N 29/02* | (2006.01) |
| *G01N 5/04* | (2006.01) |
| *G01N 17/00* | (2006.01) |

(52) U.S. Cl.
CPC .......... *G01N 29/036* (2013.01); *G01N 5/04* (2013.01); *G01N 17/00* (2013.01); *G01N 29/022* (2013.01); *G01N 29/22* (2013.01); *G01N 2291/014* (2013.01); *G01N 2291/021* (2013.01); *G01N 2291/0255* (2013.01); *G01N 2291/0256* (2013.01); *G01N 2291/0426* (2013.01); *Y10T 29/49155* (2015.01)

(58) Field of Classification Search
CPC .... G01N 29/036; G01N 29/22; G01N 29/022; G01N 2291/014; G01N 2291/021; G01N 2291/0255; G01N 2291/0256; G01N 2291/0426; G01N 5/04; G01N 17/00
See application file for complete search history.

(56) References Cited

U.S. PATENT DOCUMENTS

| | | |
|---|---|---|
| 5,187,458 A | 2/1993 | Yamashita et al. |
| 5,528,806 A | 6/1996 | Yamashita et al. |
| 5,740,595 A | 4/1998 | Yamashita et al. |
| 5,751,200 A | 5/1998 | Yamashita et al. |
| 2011/0061462 A1* | 3/2011 | Ichihashi ............... G01N 9/002 73/579 |

FOREIGN PATENT DOCUMENTS

| | | |
|---|---|---|
| GB | 2285508 | 7/1995 |
| JP | 59-067709 | * 4/1984 |

(Continued)

OTHER PUBLICATIONS

CNOA—Office Action of corresponding Chinese Patent Application No. 201280075178.1 dated Aug. 19, 2016, with full English translation.

(Continued)

*Primary Examiner* — Daniel S Larkin
(74) *Attorney, Agent, or Firm* — Fujitsu Patent Center

(57) ABSTRACT

In a QCM sensor and a method of manufacturing the same, the QCM sensor includes: a quartz plate; and an electrode provided on one and the other principal surfaces of the quartz plate, in which the electrode is provided with a pattern having a contour line in a planar view of the electrode.

14 Claims, 31 Drawing Sheets

(56) References Cited

FOREIGN PATENT DOCUMENTS

| JP | 3-108806 |   | 5/1991 |
|----|----------|---|--------|
| JP | 5-296907 |   | 11/1993 |
| JP | 6-24301 |   | 3/1994 |
| JP | 7-225184 |   | 8/1995 |
| JP | 8-228123 |   | 9/1996 |
| JP | 9-250979 |   | 9/1997 |
| JP | 2001-99777 |   | 4/2001 |
| JP | 2007-104042 | * | 4/2007 |
| JP | 2009-98133 |   | 5/2009 |

OTHER PUBLICATIONS

JPOA—Office Action of Japanese Patent Application No. 2014-529226 dated May 31, 2016, with partial English translation of the Office Action.

CNOA—Office Action of Chinese Patent Application No. 201280075178.1 dated Jan. 4, 2016, with full English translation of the Office Action.

Lu Hao Zheng, "The Research of Quartz Crystal Microbalance Sensor for Indoor Air Quality Detecting" Chinese Doctoral Dissertations & Master's Theses Full-text Database (Master) Information Science and Technology, No. 3, 2005, I140-33, pp. 30-36, Jul. 15, 2005.

JPOA—Office Action of Japanese Patent Application No. 2014-529226 dated Feb. 16, 2016, with partial English translation of the Office Action.

International Search Report and Written Opinion of the International Searching Authority (Form PCT/ISA/210, Form PCT/ISA/237), mailed in connection with PCT/JP2012/070520 and dated Oct. 23, 2012 (7 pages). Partial English Translation.

CNOA—Office Action of corresponding Chinese Patent Application No. 201280075178.1 dated Feb. 4, 2017, with English translation.

CNOA—Office Action of Chinese Patent Application No. 201280075178.1 dated Oct. 9, 2017, with partial translation of the Office Action.

\* cited by examiner

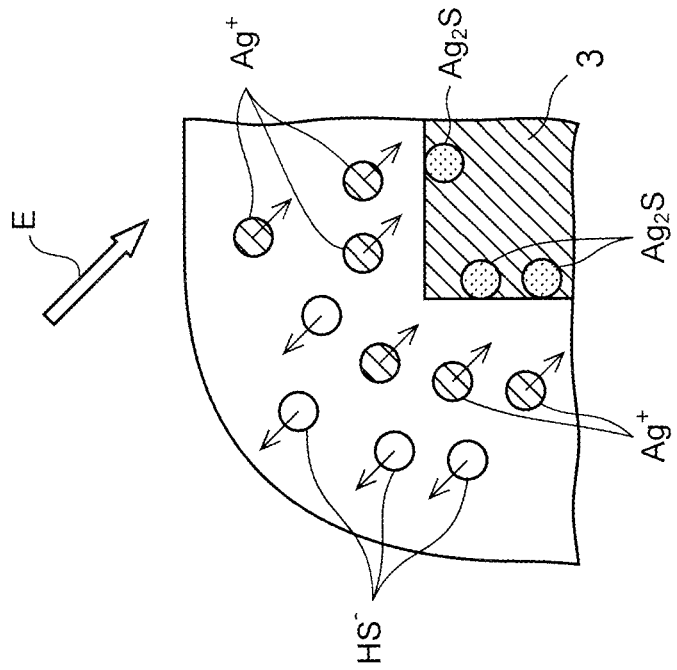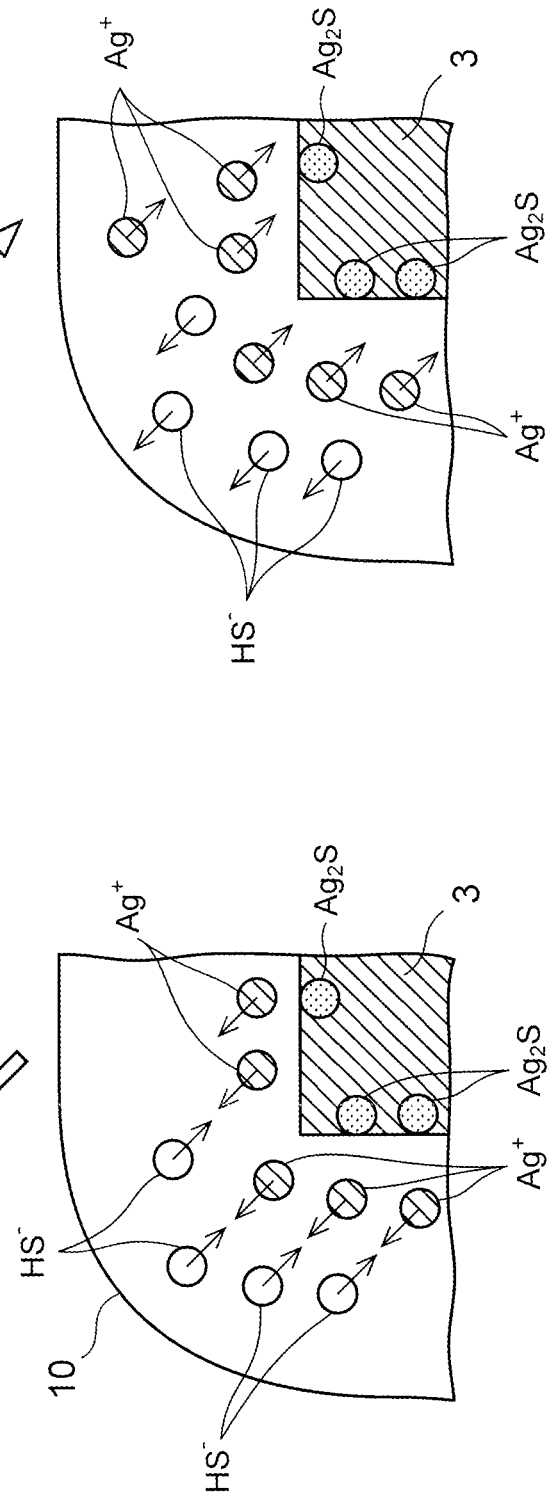

QCM SENSOR AND METHOD OF MANUFACTURING THE SAME

CROSS-REFERENCE TO RELATED APPLICATION

This application is a continuation of International Patent Application No. PCT/JP2012/070520 filed Aug. 10, 2012 and designated the U.S., the entire contents of which are incorporated herein by reference.

FIELD

The embodiments discussed herein are related to a QCM sensor and a method of manufacturing the same.

BACKGROUND

Various corrosive gases such as a hydrogen sulfide gas are contained in the atmosphere in a living environment. Even with low concentrations, the corrosive gases corrode electronic equipment or the like and accelerate its deterioration. Monitoring the corrosive gases in an environment where the electronic equipment is placed is effective in grasping the influence of the corrosive gases on the electronic equipment.

A QCM sensor is one of corrosion sensors for monitoring corrosive gases. The QCM sensor includes a quartz plate provided with electrodes on both principal surfaces, and is configured to oscillate the quartz plate at a natural oscillation frequency by applying a predetermined voltage to the electrodes under actual use conditions.

The above-described natural oscillation frequency decreases along with an increase in mass of the electrodes of the QCM sensor due to corrosion by the corrosive gases. Thus, the approximate amount of the corrosive gases contained in the environment may be monitored by measuring the amount of decrease in the natural oscillation frequency.

Also, an improvement in sensitivity of the QCM sensor enables the QCM sensor to measure the influence of a low concentration of corrosive gases at a short time.

Patent Document 1: Japanese Laid-open Patent Publication No. 05-296907
Patent Document 2: Japanese Laid-open Patent Publication No. 08-228123
Patent Document 3: Japanese Examined Laid-open Patent Publication No. Hei 06-24301

SUMMARY

According to one aspect of the disclosure given below, there is provided a QCM sensor including: a quartz plate; and an electrode provided on each of one and the other principal surfaces of the quartz plate, in which the electrode is provided with a pattern having a contour line in a planar view of the electrode.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 5A and 5B are enlarged sectional views illustrating in schematic form movements of ions on the periphery of the electrode of the QCM sensor;

DESCRIPTION OF EMBODIMENTS

Figure 1A:
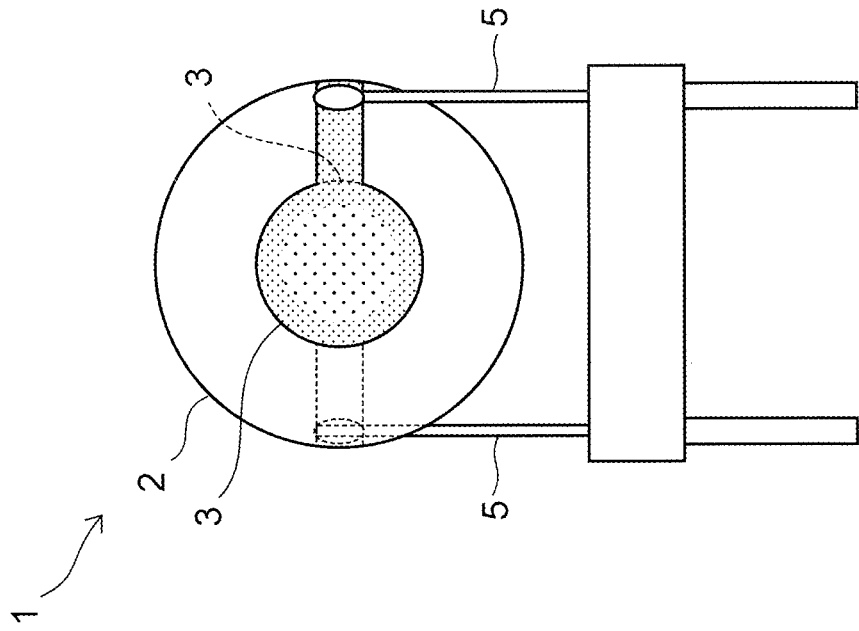
FIG. 1A is a planar view of a new QCM sensor before corrosion.

Prior to description of embodiments, description will be given with regard to results of discussions made by the inventor.

An oscillation frequency of a QCM sensor decreases with increasing mass of electrodes as mentioned above, and it is known that the amount of decrease in the oscillation frequency is proportional to the amount of increase in the mass of the electrodes according to Sauerbrey equation. When this is utilized, in case of, for example, a QCM sensor having an oscillation frequency of 9 MHz, a 1-Hz decrease in the oscillation frequency corresponds to a 1-ng increase in the mass of the electrodes, thus enabling high-sensitivity measurement of the influence of corrosive gases.

Here, methods for further improvement of the sensitivity of the QCM sensor may include the approach of roughening a surface of each electrode. According to the approach, an increase in an area of contact between the surface of the electrode and the corrosive gases takes place and thus leads to a large amount of increase in the mass of the electrode due to corrosion and hence to a large amount of change in the oscillation frequency with increasing mass, thus enabling achievement of an increase in the sensitivity of the QCM sensor.

However, it is technically difficult to selectively roughen the surface alone of the electrode as mentioned above without affecting other portions of the QCM sensor. For example, the surface of the electrode may be subjected to mechanical grinding or chemical etching to roughen the surface of the electrode; however, in this case, a quartz plate or the like around the electrode is also subjected to the grinding or the etching, and thus, characteristics of the QCM sensor deviate from specifications.

Also, a fundamental oscillation frequency of the QCM sensor may be increased to achieve an increase in the sensitivity. An increase in the mass of the electrode is proportional to the oscillation frequency according to the above-mentioned Sauerbrey equation, and therefore, the oscillation frequency is increased in this manner, and thereby, even a slight increase in the mass causes a large change in the oscillation frequency and thus enables achieving an increase in the sensitivity of the QCM sensor.

However, stable oscillation of the QCM sensor needs the use of an appropriate oscillator circuit according to the magnitude of the fundamental oscillation frequency, and thus, it is difficult for a single oscillator circuit to cover low- to high-frequency ranges. Moreover, it is known that in the QCM sensor, the higher the fundamental oscillation frequency, the lower the stability, and an upper limit of the fundamental oscillation frequency is considered to be of the order of 30 MHz.

Description will be given below with regard to a QCM sensor capable of achieving an increase in the sensitivity without roughening the surface of the electrode or increasing the fundamental oscillation frequency as described above.

EMBODIMENTS

In the embodiment, attention will be given to a mechanism of corrosion of an electrode of a QCM sensor, as described below.

FIG. 1A is a planar view of a new QCM sensor before corrosion.

A QCM sensor 1 includes an AT-cut quartz plate 2, an electrode 3 formed on each of one and the other principal surfaces of the quartz plate 2, and a lead wire 5 connected to the electrode 3 by conductive paste 4.

The lead wire 5 is fixed to a socket 6, and the socket 6 is provided with a terminal 7 connected to the lead wire 5. Also, a material for the electrode 3 is silver in this example.

In such a new QCM sensor 1, the electrode 3 is not corroded and assumes a lustrous white color inherent therein.

Figure 1B:
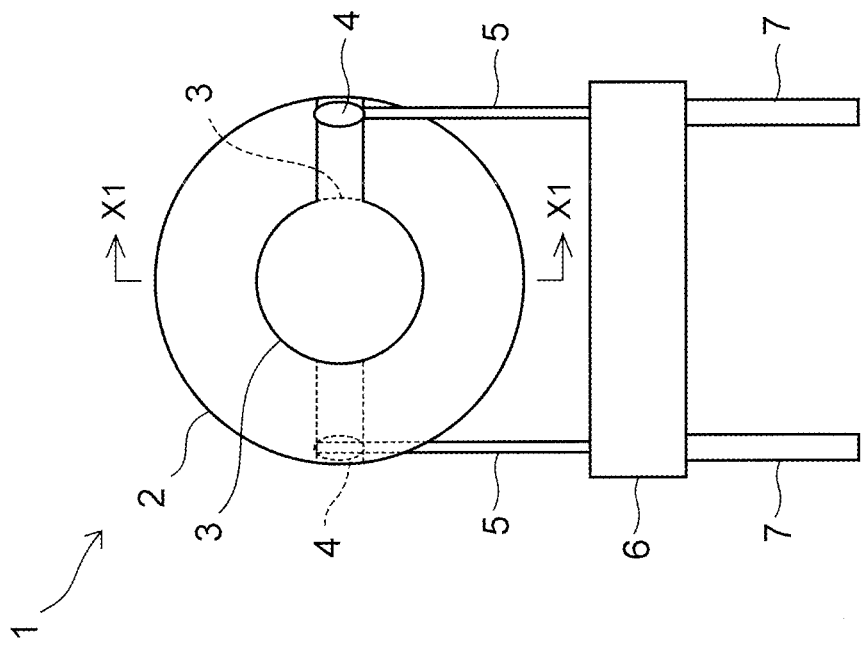
FIG. 1B is a planar view of the QCM sensor after the corrosion.

Meanwhile, FIG. 1B is a planar view of the QCM sensor 1 after the corrosion.

As illustrated in FIG. 1B, after the corrosion, the electrode 3 assumes a blackish brown color due to rust.

Then, a detailed observation of the QCM sensor 1 demonstrates that the electrode 3 changes markedly in its color to assume the blackish brown color in its peripheral portion rather than throughout its entire area, whereas the electrode 3 remains somewhat lustrous in the vicinity of its center.

It has become apparent from this result that the corrosion of the electrode 3 does not occur uniformly in the surface thereof but advances more rapidly in the peripheral portion thereof than in a central portion thereof.

Figure 2:
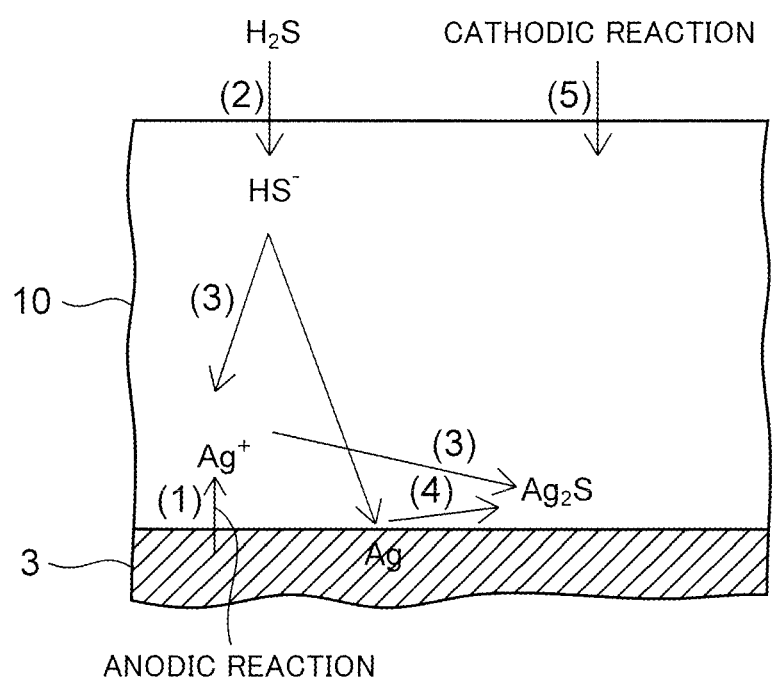
FIG. 2 is a cross-sectional view illustrating in schematic form a mechanism of corrosion of an electrode of the QCM sensor.

FIG. 2 is a cross-sectional view illustrating in schematic form the mechanism of the corrosion of the electrode 3. Note that FIG. 2 is the view assuming that silver is used as the material for the electrode 3 and is corroded by $H_2S$ gas.

Water in the atmosphere is adsorbed on the surface of the electrode 3 to form a water membrane 10 thereon. Although a thickness of the water membrane 10 varies according to humidity of the atmosphere, a substance adsorbed on the electrode 3, and a surface condition of the electrode 3, the thickness is of the order of several nanometers to several tens of nanometers.

In the water membrane 10, reactions corresponding to Equations (1) to (5), respectively, proceed.

First, the silver of the electrode 3 is ionized to dissolve in the water membrane 10, as represented by Equation (1).

[Equation 1]

$$2Ag \rightarrow 2Ag^+ + 2e^- \qquad (1)$$

The reaction expressed by Equation (1) is called an anodic reaction.

Also, the $H_2S$ gas dissolves in the water membrane 10 to generate $HS^-$ ions as represented by Equation (2).

[Equation 2]

$$H_2S + H_2O \rightarrow HS^- + H_3O^- \qquad (2)$$

The HS⁻ ions become a cause of corrosion of the silver, and the corrosion of the silver by the HS⁻ ions is of two types of routes as given below.

The first route is as follows; specifically, the HS⁻ ions react directly with Ag⁺ ions dissolved by an anode thereby to yield $Ag_2S$ as a corrosion product on the electrode 3, as represented by Equation (3).

[Equation 3]

$$HS^- + 2Ag^+ \rightarrow Ag_2S + H^+ \quad (3)$$

Then, the second route is as follows; specifically, the HS⁻ ions are adsorbed on the surface of the electrode 3 as the anode to yield $Ag_2S$ as a corrosion product, as represented by Equation (4).

[Equation 4]

$$HS^- + H^+ + 2Ag \rightarrow Ag_2S + H_2 \quad (4)$$

Note that a reaction at a cathode is dissolution of $O_2$ in the atmosphere in the water membrane 10, which is represented by Equation (5).

[Equation 5]

$$\frac{1}{2}O_2 + H_2O + 2e^- \rightarrow 2OH^- \quad (5)$$

The corrosion product, i.e. $Ag_2S$, produced by the reactions represented as Equations (3) and (4) is the rust on the electrode 3 illustrated in FIG. 1B.

From Equations (3) and (4), it may also be seen that a rate at which the corrosion produces the corrosion product, i.e. $Ag_2S$, is determined by factors including the respective concentrations of the Ag⁺ ions and the HS⁻ ions in the water membrane 10, and a rate of diffusion of these ions in the water membrane 10.

Here, the rate of corrosion in the QCM sensor may also depend on an electric field produced in the QCM sensor in process of being driven, as will be described below, besides the above-described factors.

Figure 3:
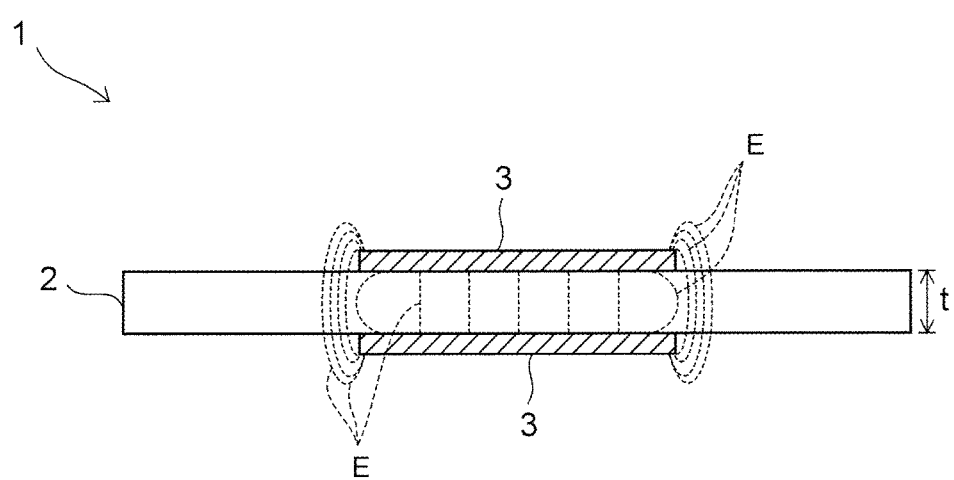
FIG. 3 is a cross-sectional view taken along line X1-X1 of FIG. 1A.

FIG. 3 is a cross-sectional view taken along line X1-X1 of FIG. 1A.

As illustrated in FIG. 3, the electrodes 3 face each other with the quartz plate 2 in between, and have a structure similar to that of a capacitor.

The intensity of an electric field E produced in such a capacitor-like structure may be calculated in the following manner.

First, it is known that a relationship between a fundamental oscillation frequency $f_0$ of the QCM sensor 1 and a thickness t of the quartz plate 2 is established as represented by Equation (6).

[Equation 6]

$$f_0 = \frac{1670}{t} \quad (6)$$

Here, when the fundamental oscillation frequency $f_0$ of the QCM sensor 1 has a value as represented by Equation (7), Equation (8) for the thickness t is obtained from Equation (6).

[Equation 7]

$$f_0 = 25 \times 10^6 \text{ [Hz]} \quad (7)$$

[Equation 8]

$$t = \frac{1670}{25 \times 10^6} = 66.8 (\mu m) \quad (8)$$

Then, when a voltage applied between the electrodes 3 is set to 5 V, the electric field E as given by Equation (9) is produced between the electrodes 3 since a rock crystal has a dielectric constant of 4.6.

[Equation 9]

$$E = \frac{1}{4.6} \cdot \frac{5}{66.8 \times 10^{-6}} = 16.3 \times 10^3 (V/m) \quad (9)$$

The electric field E is produced more intensely in the vicinity of a periphery of each electrode 3 than in the central portion thereof, as illustrated in FIG. 3.

Figure 4:
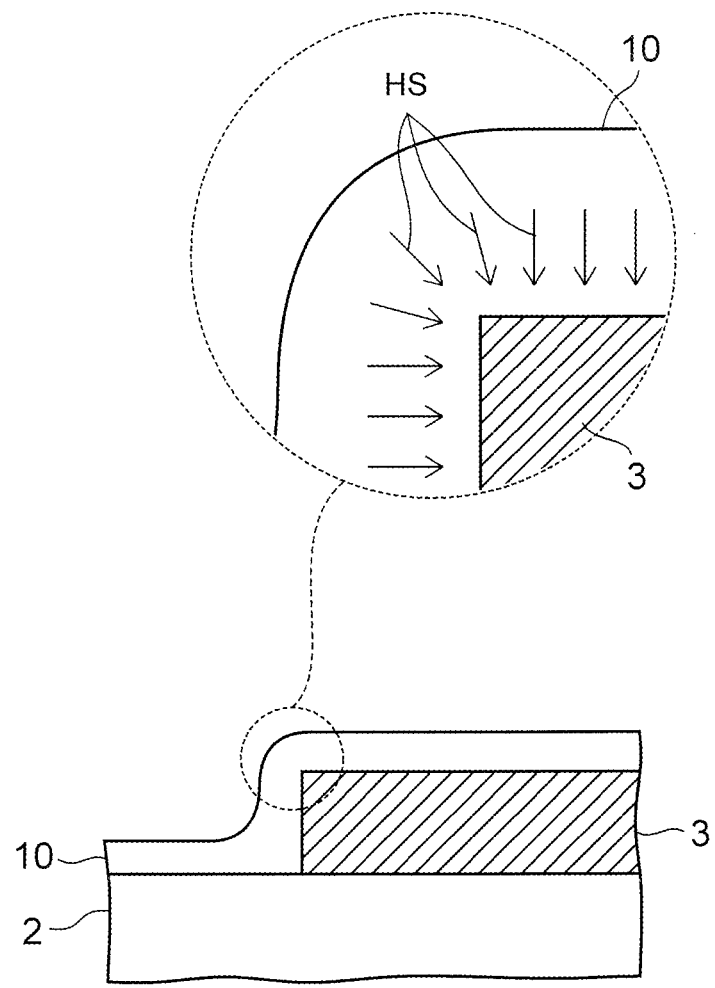
FIG. 4 is an enlarged sectional view of the vicinity of a periphery of the electrode of the QCM sensor.

FIG. 4 is an enlarged sectional view of the vicinity of the periphery of the electrode 3.

As illustrated in FIG. 4, on the periphery of the electrode 3, many HS⁻ ions are fed to the surface of the electrode 3 by the strong electric field E as described above, thus accelerating corrosion on the surface.

Also, FIGS. 5A and 5B are enlarged sectional views illustrating in schematic form movements of the ions on the periphery of the electrode 3.

As illustrated in FIGS. 5A and 5B, the Ag⁺ ions and the HS⁻ ions are contained in the water membrane 10 on the surface of the electrode 3, and the movements of these ions change in their directions according to the orientation of the electric field E, and the ions are disturbed by the electric field E.

For example, when the Ag⁺ ions and the HS⁻ ions move in a direction in which they move closer to each other by the electric field E as illustrated in FIG. 5A, the Ag⁺ ions and the HS⁻ ions encounter each other to, there, yield the corrosion product, i.e. $Ag_2S$, and the ions become electrically neutral.

Meanwhile, as illustrated in FIG. 5B, when the electric field E reverses its direction, the Ag⁺ ions and the HS⁻ ions which have not yielded $Ag_2S$ move in a direction in which they move away from each other, and then, when the electric field E reverses its direction again, these ions may produce the corrosion product, i.e. $Ag_2S$, as described above.

Thus, the electric field E acts to disturb unreacted ions and hence accelerate their reaction. This effect is particularly noticeable in the peripheral portion of the electrode 3 at which the electric field E concentrates, and this may become one of causes to produce a difference in progress of the corrosion illustrated in FIG. 1B.

Next, description will be given with regard to the influence of such acceleration of the corrosion by the electric field E on Sauerbrey equation.

Sauerbrey equation for the QCM sensor 1 is represented by Equation (10).

[Equation 10]

$$\Delta f = \frac{f_q^2 M_f}{N \rho_q S} \quad (10)$$

Values in Equation (10) are defined as given below.
Δf: the amount of change in the oscillation frequency
$f_q$: the fundamental oscillation frequency
$\rho_q$: density of the quartz plate 2
N: a constant which depends on the cut of the quartz plate 2
S: the total area of the electrode 3
$M_f$: the mass of the corrosion product In the right side of Equation (10), $f_q^2/(N\rho_q)$ denotes a constant determined by the quartz plate 2 and the fundamental oscillation frequency $f_q$, and $M_f/S$ denotes the mass of the corrosion product on the electrode 3 per unit area. According to Sauerbrey equation, therefore, the amount Δf of change in the oscillation frequency has no relation to the total area of the electrode 3.

The inventor has performed the following examination in order to confirm this.

Figure 6A:
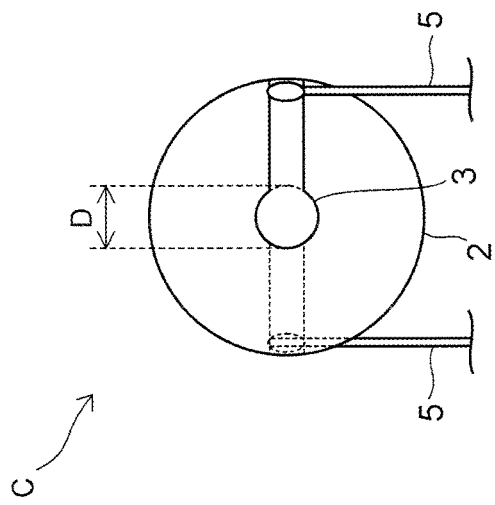
FIGS. 6A to 6C are planar views of QCM sensors used in examination.
Figure 6B:
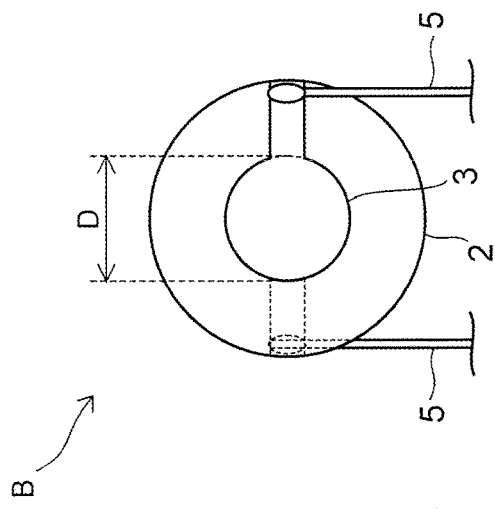
Figure 6C:
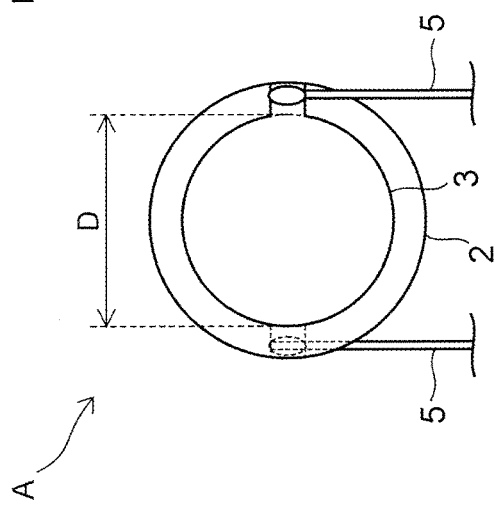

FIGS. 6A to 6C are planar views of three QCM sensors having the electrodes having different areas, respectively, used in the examination. In the examination, three QCM sensors A to C having the substantially circular electrodes 3 having diameters D of 7.0 mm (see FIG. 6A), 3.5 mm (see FIG. 6B), and 2.4 mm (see FIG. 6C), respectively, are placed in the same atmosphere. Note that a temperature in the atmosphere is set to 23° C.

Further, $H_2S$ gas, $SO_2$ gas and $NO_2$ gas are added as corrosive gases to the atmosphere. In the atmosphere, the concentrations of the corrosive gases are as follows: the $H_2S$ gas has a concentration of 0.25 ppm; the $SO_2$ gas, 0.15 ppm; and the $NO_2$ gas, 0.13 ppm.

Also, dry nitrogen having a humidity of about 0% is introduced into the atmosphere, while humidity in the atmosphere is maintained at 50% by performing humidity control on the above-described corrosive gases.

Figure 7:
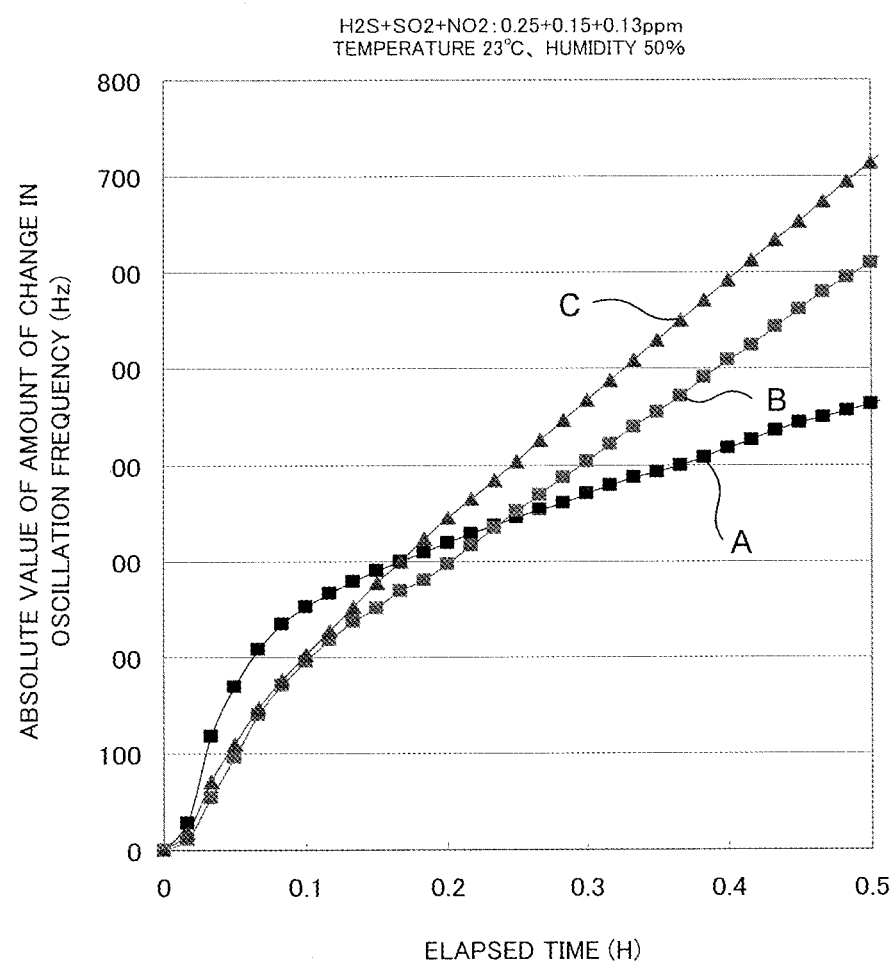
FIG. 7 is a graph obtained by examining the absolute value of the amount of change in an oscillation frequency of each of the QCM sensors.

FIG. 7 is a graph illustrating the absolute value of the amount of change in the oscillation frequency when each of the QCM sensors A to C of FIGS. 6A to 6C is exposed in the atmosphere.

In FIG. 7, the horizontal axis indicates elapsed time since the exposure of the QCM sensors A to C in the above-described atmosphere, and the vertical axis indicates the amount of change in the oscillation frequency of each of the QCM sensors A to C.

As illustrated in FIG. 7, the QCM sensors A to C all increase sharply in the amount of change in the oscillation frequency immediately after the exposure in the atmosphere, which is caused by formation of the above-described water membrane 10 (see FIG. 2). At this time, the corrosion of the electrode 3 has not started yet.

The corrosion of the electrode 3 starts after 0.1 h, and at this time, the gradients of graphs vary from one to another of the QCM sensors A to C. This is different from the above-described conclusion that according to Sauerbrey equation, the amount Δf of change in the oscillation frequency has no relation to the total area of the electrode 3.

The inventor has made discussions as to why such a difference arises, as given below.

First, when $f_q^2/(N\rho_q)$ in the right side of Equation (10) is represented as K, Sauerbrey equation is expressed by the following equation: Δf=−KΔM, where ΔM=$M_f$/S.

Figure 8:
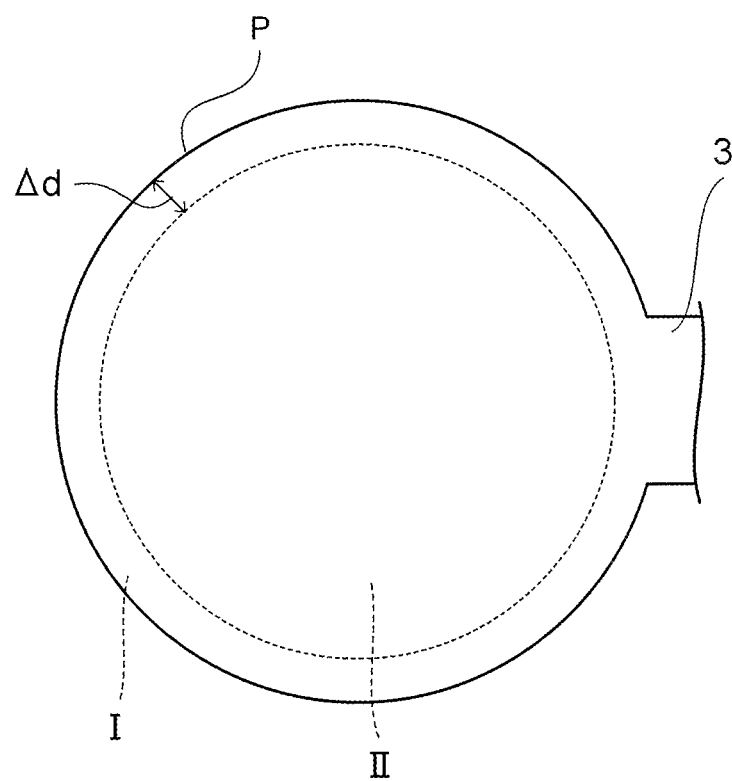
FIG. 8 is a planar view illustrating an edge portion and a surface portion of the electrode of the QCM sensor.

Then, as illustrated in a planar view of FIG. 8, a peripheral region of the electrode 3 where corrosion advances more rapidly than that in other portions is defined as an edge portion I, and the remaining portion is defined as a surface portion II.

Although the edge portion I is not particularly limited, erosion proceeds noticeably in a region at a distance less than a film thickness of the electrode 3 as measured from a contour line P of the electrode 3 when seen in a planar view, and it is therefore preferable that a region inward of the contour line P by a distance Δd equal to or greater than the film thickness from the contour line P be set to the edge portion I. In this example, a region at a distance Δd on the order of 0.1 to 0.5 mm is set to the edge portion I.

Then, when ΔM is further rewritten by using the edge portion I and the surface portion II, Sauerbrey equation may be transformed into a form as represented by Equation (11).

[Equation 11]

$$\Delta f = K \frac{\text{(the amount of corrosion of the surface portion II)} + \text{(the amount of corrosion of the edge portion I)}}{\text{the total area of the electrode 3}} \quad (11)$$

$$= K \left\{ \text{(the amount of corrosion of the electrode 3 per unit area)} + \frac{\text{(the amount of corrosion of the edge portion I)}}{\text{(the total area of the electrode 3)}} \right\}$$

Note that the amounts of corrosions in Equation (11) indicate the masses of the electrode 3 increased by the corrosions, and the total amount of the masses is equal to $M_f$ in Equation (10).

A first term inside parentheses in the right side of Equation (11) indicates the amount of corrosion of the electrode 3 per unit area, and this value has no relation to the size of the electrode 3.

Meanwhile, a second term inside the same parentheses indicates a value taking into account the edge portion I in which the corrosion advances more rapidly as compared to that in the other portions, and it is conceivable that an effect of this term leads to the amount Δf of change in the oscillation frequency having a value varying according to the total area of the electrode 3, as illustrated in FIG. 7.

The above-described second term indicates such an effect of the edge portion I on the amount Δf of change. Then, the amount Δf of change serves as an index indicating to what extent the QCM sensor responds sensitively to the corrosive gases, so that the amount Δf of change may be used as the sensitivity of the QCM sensor.

Also, the longer the contour line P of the electrode 3, the larger (the amount of corrosion of the edge portion I) in a numerator in the second term in Equation (11). In the embodiment, therefore, the sensitivity of the QCM sensor is estimated from a ratio R given by Equation (12), based on analogy with the second term.

[Equation 12]

$$R = \frac{L}{S} \quad (12)$$

In Equation (12), S denotes the total area of the electrode 3, and L denotes the length of the contour line P of the electrode 3.

The ratio R is obtained by substituting the length L of the contour line P for (the amount of corrosion of the edge portion I) in the numerator in the second term inside the parentheses in the right side of Equation (11), and the sensitivity may be directly expressed based on S and L representing geometrical features of the electrode 3.

Here, when the ratio (L/S) of Equation (12) is calculated for each of the three QCM sensors A to C (see FIGS. 6A to 6C) used in the examination of FIG. 7, calculated results are as follows.

The QCM sensor A $$L/S=(7\times3.14)/(3.5\times3.5\times3.14)=0.57$$

The QCM sensor B $$L/S=(3.5\times3.14)/(1.75\times1.75\times3.14)=1.14$$

The QCM sensor C $$L/S=(2.4\times3.14)/(1.2\times1.2\times3.14)=1.67$$

Thus, the QCM sensor A, the QCM sensor B and the QCM sensor C, in this order, become larger in the ratio L/S and hence higher in their sensitivity, which is consistent with the examined result that the QCM sensor A, the QCM sensor B and the QCM sensor C, in this order, become larger in the amount Δf of change in the oscillation frequency, as illustrated in FIG. 7.

Figure 9:
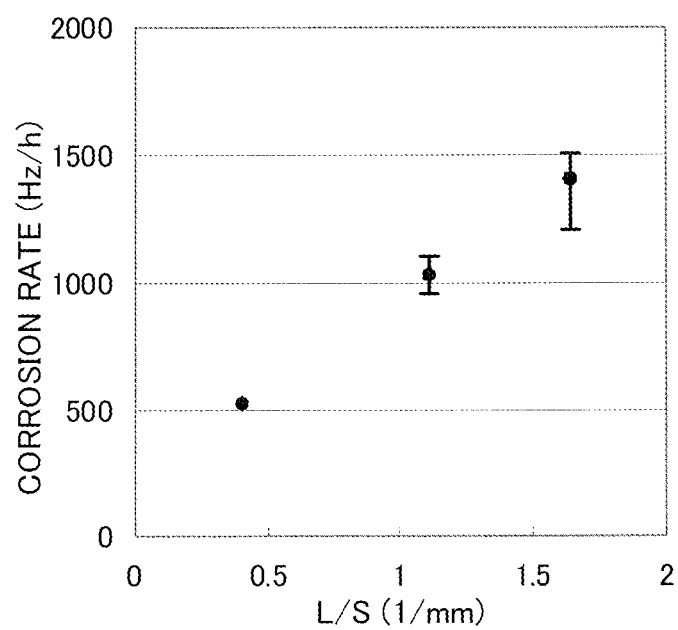
FIG. 9 is a graph obtained by examining the corrosion rates of the electrodes of the QCM sensors.

FIG. 9 is a graph obtained by examining the corrosion rates of the electrodes 3 provided in the above-described QCM sensors A to C.

Note that the corrosion rate refers to the amount Δf of change in the oscillation frequency of each of the QCM sensors A to C per unit time. Also, in FIG. 9, the horizontal axis indicates the above-described ratio L/S.

In the examination, the QCM sensors A to C are exposed in an atmosphere in which the temperature, the humidity and the concentrations of the corrosive gases are set under the same conditions.

As illustrated in FIG. 9, the larger the ratio L/S, the rapider the corrosion rate. This indicates that in the same atmosphere, the QCM sensor having the larger ratio L/S is more sensitive to corrosive properties of the atmosphere and hence is higher in its sensitivity.

It has become apparent from the above result that the ratio L/S may be set as high as possible in order to enhance the sensitivity of the QCM sensor.

In order to increase the ratio L/S, it is preferable that a pattern having the longest possible contour line when seen in a planar view be formed on the electrode 3 so that the electrode 3 is provided with the largest possible edge portion in which the corrosion proceeds easily.

Note that the total area S of the electrode 3 may also be reduced in order to increase the ratio L/S. With this approach, however, the QCM sensor becomes high in its crystal impedance and hence unstable in its oscillation, and it is therefore preferable that the length L be increased to increase the ratio L/S, as described above.

Description will be given below with regard to examples of the QCM sensor according to the embodiment having the sensitivity increased by increasing the ratio L/S in the manner as above described.

First Example

Figure 10A:
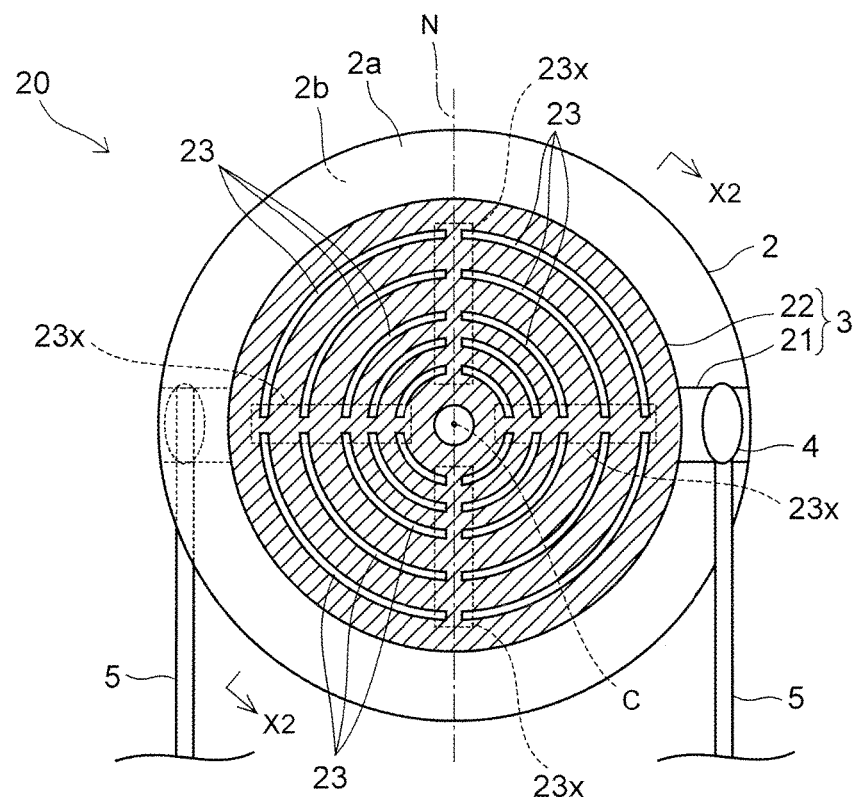
FIG. 10A is a planar view of a QCM sensor according to a first example of an embodiment.
Figure 10B:
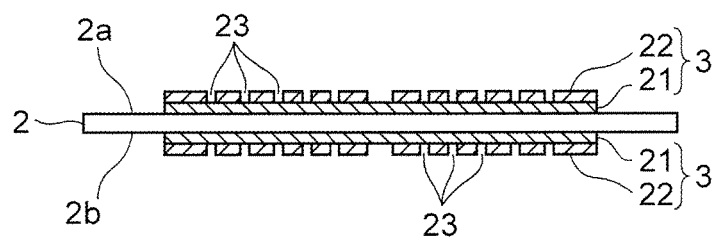
FIG. 10B is a cross-sectional view taken along line X2-X2 of FIG. 10A.

FIG. 10A is a planar view of a QCM sensor 20 according to a first example, and FIG. 10B is a cross-sectional view taken along line X2-X2 of FIG. 10A.

In the example, as illustrated in FIG. 10B, a first metal film 21 and a second metal film 22 are stacked in this sequence on the quartz plate 2 thereby to form the electrode 3.

Note that the electrode 3 is formed not only on one principal surface 2a of the quartz plate 2 but also on the other principal surface 2b of the quartz plate 2.

Also, a material which is lower in its reactivity to the corrosive gases than that for the second metal film 22 is used as a material for the first metal film 21. In the example, gold is used as the material for the first metal film 21.

By using the material having the lower reactivity to the corrosive gases as described above, the first metal film 21 does not corrode but remains on the quartz plate 2 even if the second metal film 22 corrodes completely away. Thus, the first metal film 21 alone may ensure a function of the electrode 3, and a voltage may be applied to the electrode 3 to oscillate the QCM sensor 20 even after the second metal film 22 has corroded completely away.

Meanwhile, a material which is higher in its reactivity to the corrosive gases as compared to that for the first metal film 21 is used as the material for the second metal film 22. Although the material may be selected according to the corrosive gas as an object to be monitored, in the example, silver is used as the material for the second metal film 22.

Thereby, the second metal film 22 is moderately corroded by the corrosive gases, thus enabling good monitoring of the corrosive gases.

Also, in the example, as illustrated in FIG. 10A, the second metal film 22 of the electrode 3 is provided with plural slits 23 as the pattern for increasing the above-described ratio (L/S).

The slits 23 are not particularly limited in plan configuration. In the example, the slits 23 are provided in an arcuate shape concentric with a center C of the electrode 3.

The slits 23 are arcuately shaped as described above, and thereby, connection portions 23x without the slits 23 are formed in the second metal film 22. The connection portions 23x connect all portions of the second metal film 22 together and thus enable reducing the risk of the second metal film 22 peeling wholly off from the first metal film 21 even if corrosion of the second metal film 22 proceeds and deteriorates adhesion between the metal films 21, 22.

Further, in the example, the electrode 3 provided on the one principal surface 2a of the quartz plate 2 and the electrode 3 provided on the other principal surface 2b of the quartz plate 2 have the same slits 23 in the planar view of the electrodes 3. Thus, the electrodes 3 are the same in terms of the pattern for increasing the ratio (L/S), and thereby, the electrodes 3 may oscillate the quartz plate 2 with stability when the voltage is applied to the electrodes 3.

Preferably, the degree of geometrical symmetry of the slits 23 is set as high as possible in order to improve the stability of oscillation. In the example, as illustrated in FIG. 10A, the slits 23 have an axis of symmetry N in a plane of the electrode 3 and achieve a high degree of geometrical symmetry of the slits 23 and thus may achieve the stability of oscillation as described above. In this respect, the same goes for a second example and a third example to be described later.

Figure 11:
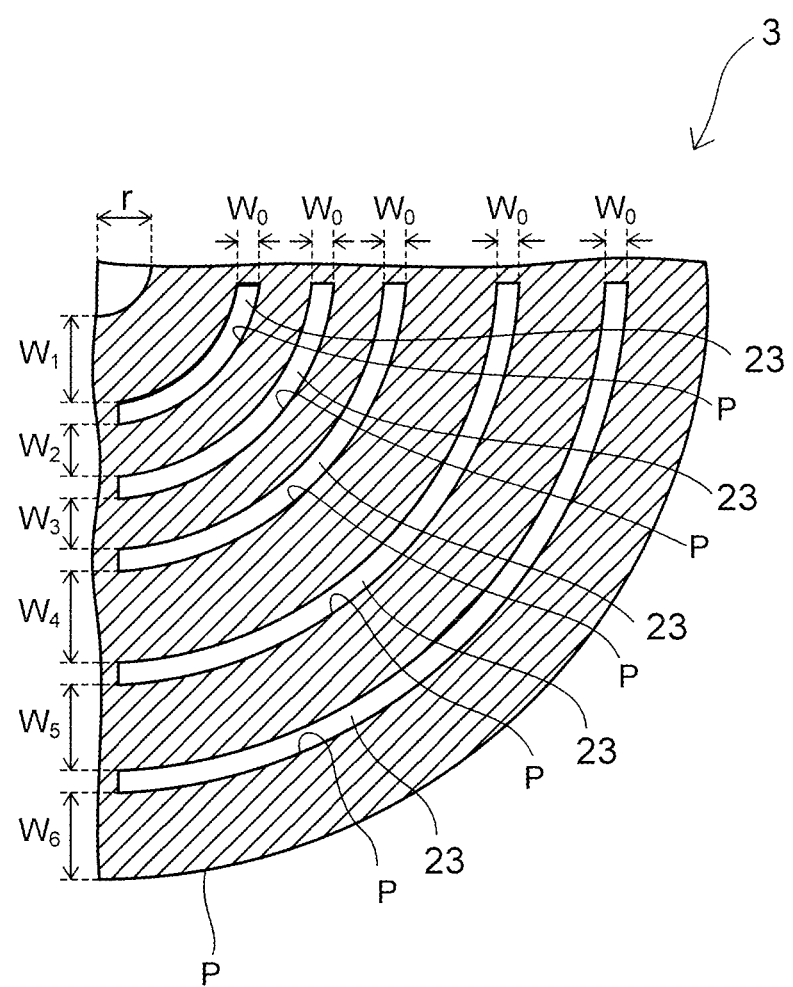
FIG. 11 is an enlarged planar view of the electrode provided in the QCM sensor according to the first example of the embodiment.

FIG. 11 is an enlarged planar view of the electrode 3.

As illustrated in FIG. 11, the slits 23 are provided thereby to form plural contour lines P on the electrode 3 in the planar view. This increases the total sum L of the lengths of the contour lines P and enables increasing the ratio L/S of Equation (12), so that the QCM sensor 20 achieves high sensitivity.

Then, calculation is performed to determine to what extent the sensitivity of the QCM sensor 20 increases as compared to that in a case where the slits 23 are absent. Note that when the calculation is performed, the connection portions 23x are ignored for sake of simplicity so that the slits 23 are in the form of concentric circles.

Also, the following values are used as the values of dimensions $W_0$ to $W_6$ in FIG. 11.

$W_0$=0.1 mm; $W_1$=0.2 mm; $W_2$=0.3 mm; $W_3$=0.4 mm; $W_4$=0.6 mm; $W_5$=0.7 mm; and $W_6$=0.7 mm.

In this case, the total sum L of the contour lines P of the electrode 3 is given by the following equation.

$$L=(0.1+0.3+0.4+0.7+0.8+1.2+1.3+1.9+2.0+2.7+2.8+3.5)\times 2\times\pi=35.4\pi \text{ (mm)}$$

Also, the total area Q of all slits 23 in the electrode 3 is given by the following equation.

$$Q=\{0.1^2+(0.4^2-0.3^2)+(0.8^2-0.7^2)+(1.3^2-1.2^2)+(2.0^2-1.9^2)+(2.8^2-2.7^2)\}\times\pi=1.42\pi$$

Then, the total area S of the electrode 3 is given by the following equation.

$$S=3.5^2\times\pi-Q=12.25\pi-1.42\pi=10.83\pi$$

Meanwhile, the total area $S_0$ of the electrode 3 without the slits 23 is given by the following equation.

$$S_0=3.5^2\times\pi=12.25\pi$$

In this case, the contour line P is formed by an outer periphery of the electrode 3, and therefore, the total length $L_0$ of the contour line P is given by the following equation.

$$L_0=3.5\times 2\times\pi=7\pi$$

Therefore, the total area S of the electrode 3 in the example is about 0.88 times (=$S/S_0$) the total area $S_0$ in the absence of the slits 23. Further, the total sum L of the lengths of the contour lines P of the electrode 3 in the example is about 5.1 times (=$L/L_0$) the total length $L_0$ in the absence of the slits 23.

Figure 12:
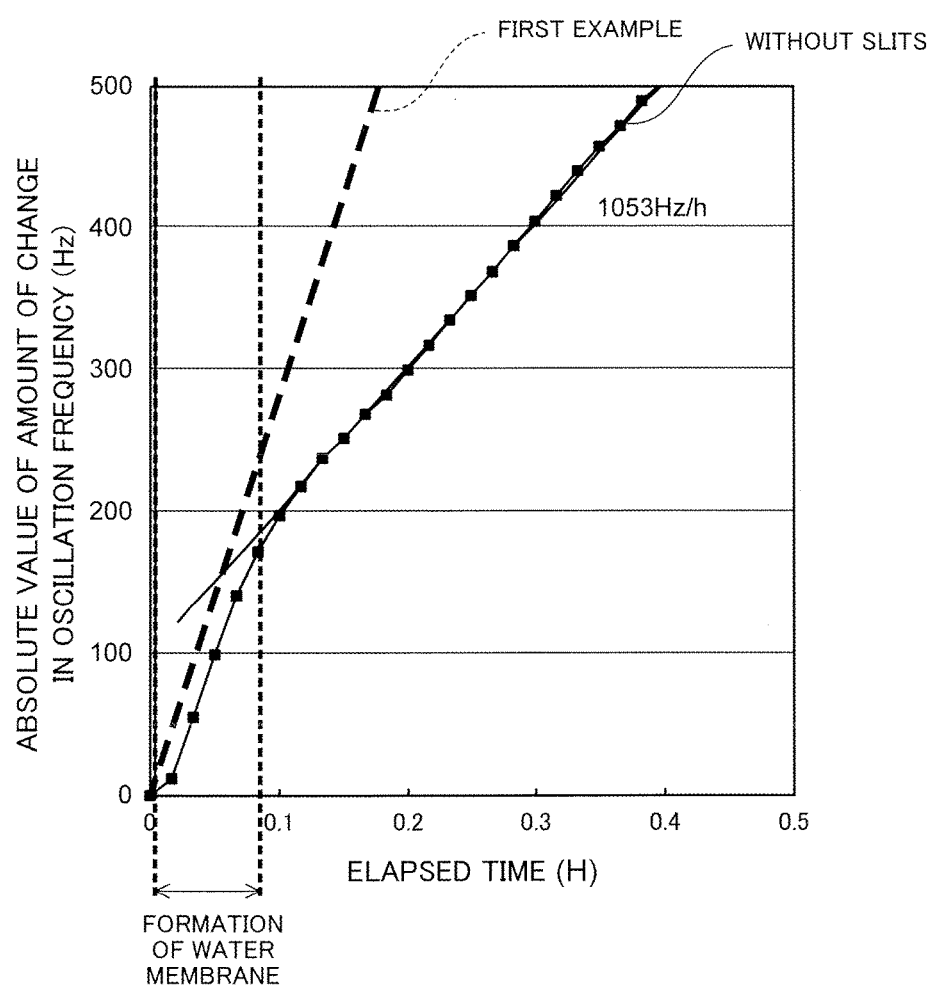
FIG. 12 is a graph obtained by examining how the amount of change in the oscillation frequency of the QCM sensor without slits 23 changes with time.

Here, examination is performed on the QCM sensor without the slits 23 to see how the absolute value of the amount Δf of change in the oscillation frequency of the QCM sensor changes with time, and in turn, results are obtained as illustrated in FIG. 12.

In FIG. 12, the vertical axis indicates the absolute value of the amount Δf of change in the oscillation frequency, and the horizontal axis indicates elapsed time since the exposure of the QCM sensor in an atmosphere containing corrosive gases.

As illustrated in FIG. 12, after a lapse of time of initial stages in which the amount Δf of change in the oscillation frequency is large due to the formation of the water membrane on the electrode, corrosion of the electrode starts and causes a slight change in the amount of increase in the amount Δf of change. At this time, the amount Δf of change per unit time is about 1053 Hz/h. At this point in time, the edge portion I (see FIG. 8) of the electrode of the QCM sensor corrodes, and therefore, corrosion of the edge portion I as well as the surface portion II of the electrode contributes to the above-described value (1053 Hz/h).

Then, the examination is further continued, and in turn, the amount Δf of change in the oscillation frequency per unit time converges to about 870 Hz/h. When the electrode is thus exposed to the corrosive gases over a long period of time, the edge portion I (see FIG. 8) of the electrode corrodes completely away, and then the corrosion proceeds slowly. Therefore, the above-described value (870 Hz/h) may be considered to be involved substantially in the corrosion of the surface portion II of the electrode.

From the results of FIG. 12, it may be seen that the edge portion I makes a contribution of 183 Hz/h (=1053 Hz/h–870 Hz/h) to the amount Δf of change in the oscillation frequency per unit time.

Using the above results, the following equation is obtained for the amount of change in the oscillation frequency of the QCM sensor 20 per unit time in a case where the QCM sensor 20 according to the example is placed in the same atmosphere as that for FIG. 12.

$$(S/S_0)\times 870 \text{ Hz/h}+(L/L_0)\times 183 \text{ Hz/h}=0.88\times 870 \text{ Hz/h}+5.1\times 183 \text{ Hz/h}=1698.9 \text{ Hz/h}$$

This indicates that the sensitivity is approximately doubled (=1698.9/870) as compared to that in the absence of the slits 23. Also, the sensitivity corresponds to sensitivity possessed by a QCM sensor having a fundamental oscillation frequency of 35 MHz.

According to the example, as described above, the electrode 3 is provided with the slits 23 as the pattern having the contour lines P thereby to enable increasing the ratio (L/S) indicating the sensitivity of the QCM sensor 20.

Thereby, the corrosion-prone edge portion becomes large in the electrode 3, so that even traces of corrosive gases cause a large change in the mass of the electrode 3 incident to corrosion and thus enable achieving an increase in the sensitivity of the QCM sensor 20.

According to the QCM sensor 20, moreover, there is nothing to roughen the surface of the electrode 3 or increase the fundamental oscillation frequency in order to achieve high sensitivity.

Further, the provision of the pattern such as the slits 23 allows the sensitivity of the QCM sensor 20 to be represented as the ratio (L/S), as described above. Thus, the sensitivity may be controlled by the total sum L of the lengths of the contour lines P or the total area S of the electrode 3, which in turn facilitates controlling the sensitivity of the QCM sensor 20.

Note that the shape of the pattern for increasing the ratio (L/S) is not limited to the above, and patterns of various shapes may be adopted as given below.

Figure 13:
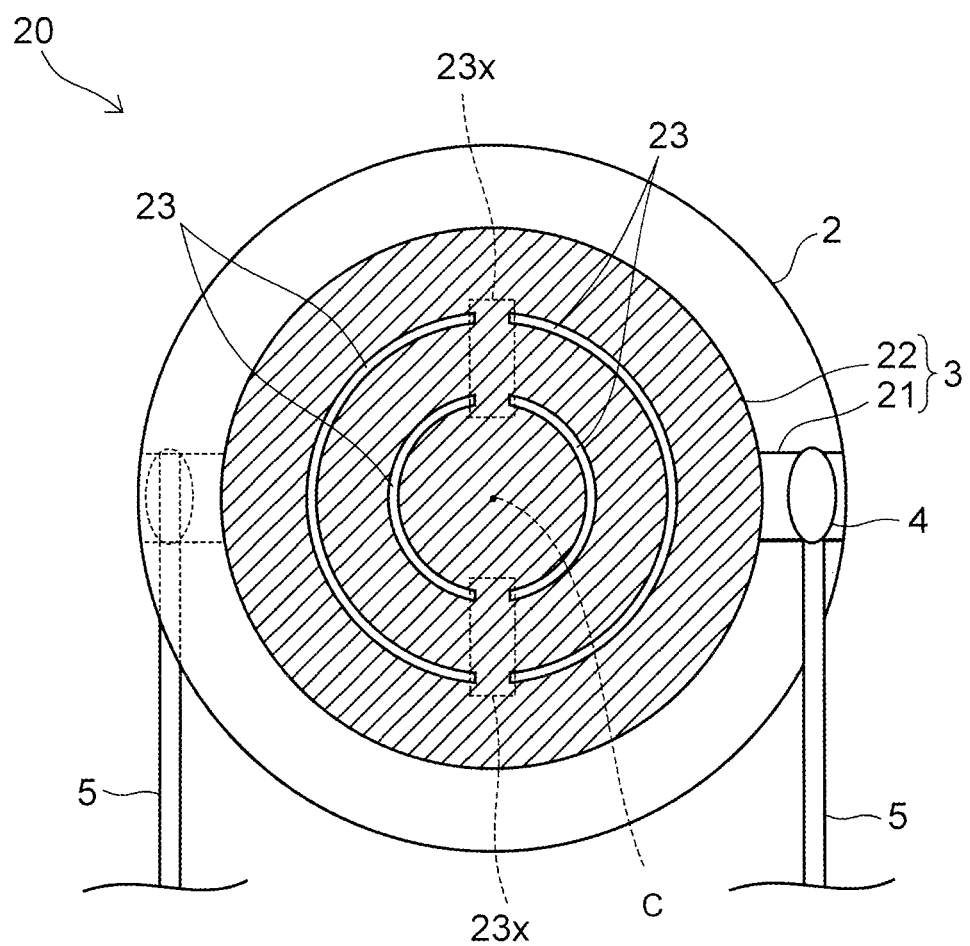
FIG. 13 is a planar view (Part 1) illustrating another example of a pattern provided on the QCM sensor according to the first example of the embodiment.
Figure 14:
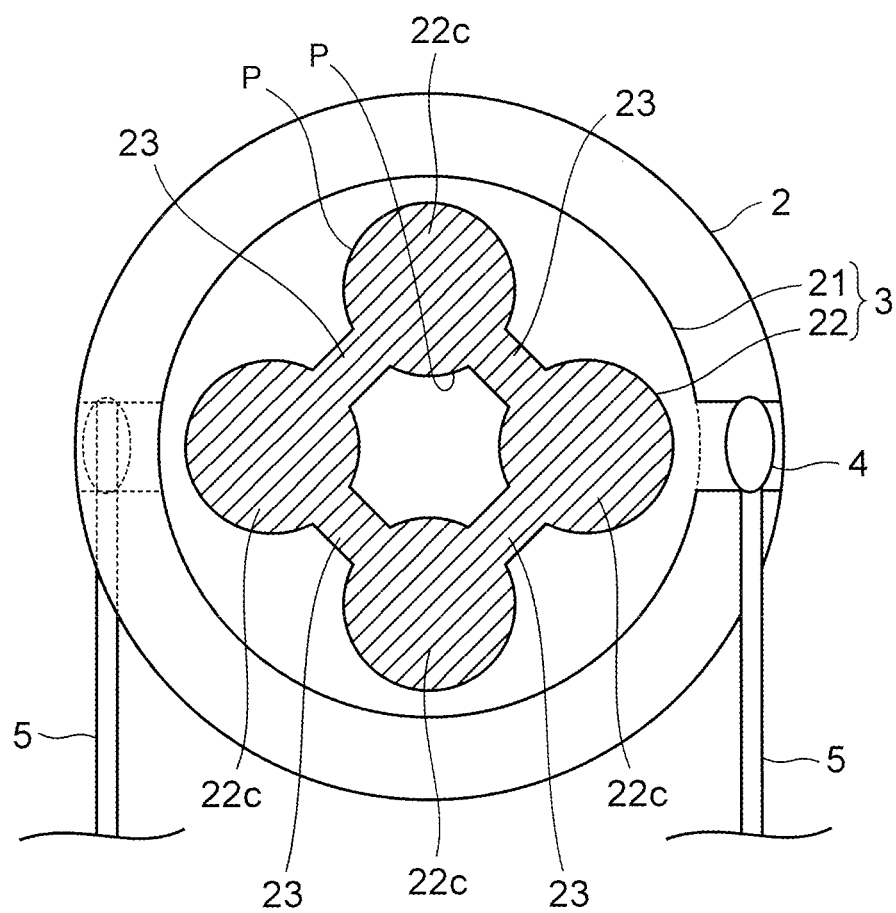
FIG. 14 is a planar view (Part 2) illustrating another example of the pattern provided on the QCM sensor according to the first example of the embodiment.

FIGS. 13 and 14 are planar views illustrating other examples of the pattern provided on the QCM sensor 20. Note that in FIGS. 13 and 14, the same structural elements as those described with reference to FIGS. 10A and 10B are designated by the same reference characters as those in these figures, and description of the same elements will be omitted hereinafter.

In the example of FIG. 13, plural slits 23 in a semi-arcuate shape concentric with the center C of the electrode 3 are provided as the pattern. Also in this case, the provision of the connection portions 23x enables preventing the peeling of the second metal film 22 on which corrosion has proceeded.

Meanwhile, in the example of FIG. 14, the second metal film 22 includes plural circular islands 22c, which are connected together by the connection portions 23x. In this case, the islands 22c form the pattern for increasing the ratio (L/S), and the sensitivity of the QCM sensor 20 may be controlled by the total sum L of the lengths of the contour lines P of the islands 22c.

Second Example

Figure 15A:
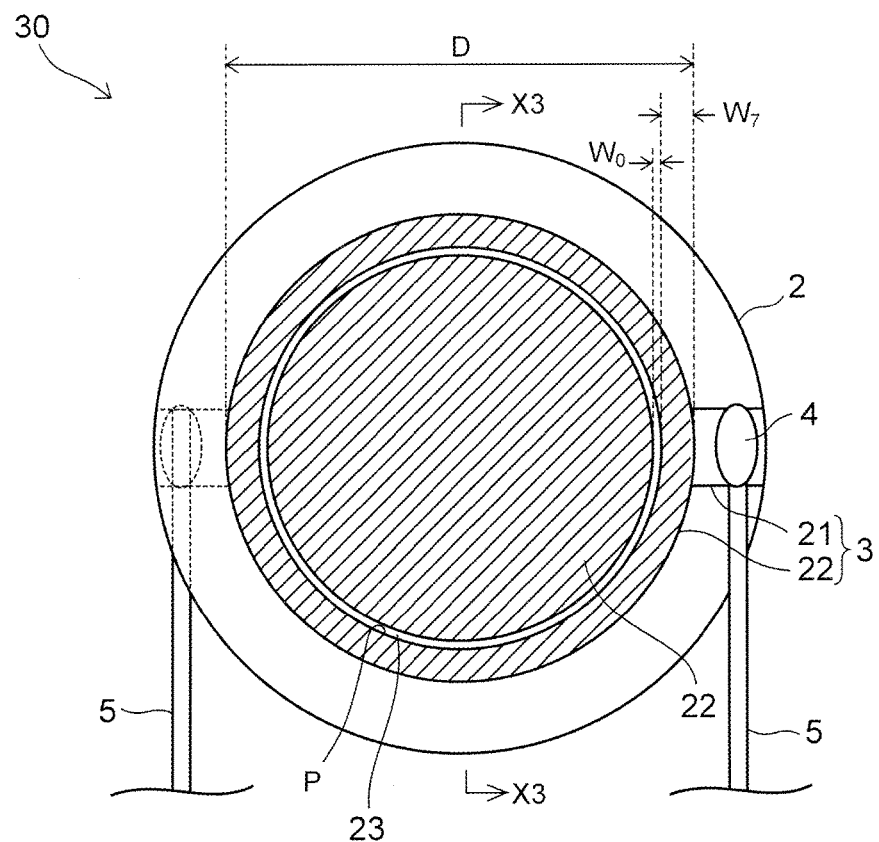
FIG. 15A is a planar view of a QCM sensor according to a second example of the embodiment.
Figure 15B:
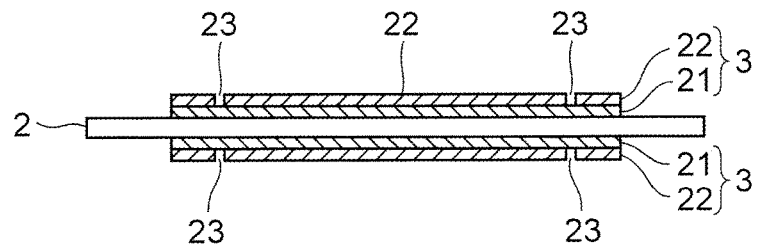
FIG. 15B is a cross-sectional view taken along line X3-X3 of FIG. 15A.

FIG. 15A is a planar view of a QCM sensor 30 according to the second example, and FIG. 15B is a cross-sectional view taken along line X3-X3 of FIG. 15A. Note that in FIGS. 15A and 15B, the same structural elements as those described with reference to FIGS. 10A and 10B are designated by the same reference characters as those in these figures, and description of the same elements will be omitted hereinafter.

In the second example, as illustrated in FIG. 15A, the slit 23 provided in the electrode 3 so as to serve as the pattern for increasing the ratio (L/S) is formed in an annular shape. Note that in the second example, the connection portions 23x (see FIG. 10A) for connecting the portions of the second metal film 22 together are not provided.

Although dimensions of the QCM sensor 30 are not particularly limited, in the second example, the width $W_0$ of the slit 23 is set to 1 mm; the distance $W_7$ from the outer periphery of the electrode 3 to the slit 23, 1 mm; and the diameter D of the electrode 3, 7 mm.

The slit 23 is provided in this manner, and thereby, as is the case with the first example, the sensitivity of the QCM sensor 30 may be increased by the total length L of the contour line P of the slit 23, and also, the sensitivity may be simply controlled by the total length L.

Next, calculation is performed to determine to what extent the sensitivity of the QCM sensor 30 is increased by the slit 23.

First, the total sum L of the lengths of the contour lines P of the slit 23 and the electrode 3 is given by the following equation.

$$3\times\pi + 5\times\pi + 7\times\pi = 15\times\pi \text{ (mm)}$$

Also, the total area ΔS of the slit 23 is given by the following equation.

$$\Delta S = 2.5^2 \times \pi + 1.5^2 \times \pi = 4 \times \pi \text{ (mm}^2\text{)}$$

Therefore, the total area of the electrode 3 is given by the following equation.

$$S = 3.5^2 \times \pi - 4 \times \pi$$

The ratio (L/S) indicating the sensitivity of the QCM sensor 30 is given by the following equation.

$$L/S = (15\times\pi)/(3.5^2\times\pi - 4\times\pi) = 1.8$$

Meanwhile, in a case where the slit 23 is not formed, the total length L of the contour line P of the electrode 3 is $7\pi$ and the total area S of the electrode 3 is $3.5^2 \times \pi$, and therefore, the ratio (L/S) indicating the sensitivity is given by the following equation.

$$L/S = 7\pi/3.5^2 \times \pi = 0.57$$

Therefore, when the slit 23 is provided, the sensitivity of the QCM sensor 30 is 3.2 times (=1.8/0.57) that in the absence of the slit 23.

Thus, also in the second example, an increase in the sensitivity of the QCM sensor may be achieved.

Here, the ratio (L/S) in a case where the slit 23 is not provided is 0.57 as described above, and therefore, the QCM sensor 30 whose sensitivity is m times that in the absence of the slit 23 may be manufactured, provided that the ratio (L/S) of the QCM sensor 30 satisfies Equation (13).

[Equation 13]

$$\frac{L}{S} = 0.57m \quad (13)$$

Figure 16:
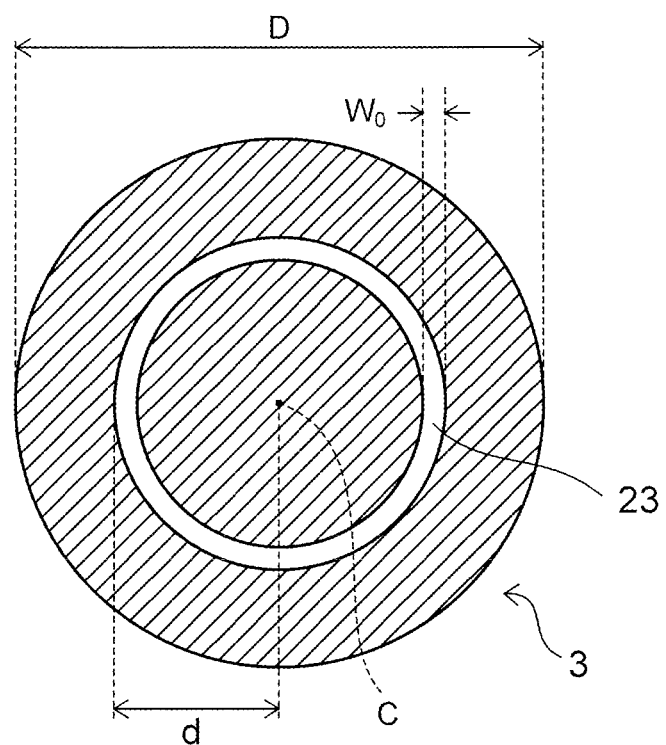
FIG. 16 is a planar view of the electrode provided in the QCM sensor designed to achieve sensitivity which is m times that in the absence of the slit, in the second example of the embodiment.

FIG. 16 is a planar view of the electrode 3 provided in the QCM sensor 30 designed to achieve m-times sensitivity as described above.

In FIG. 16, an outside diameter of the slit 23 is set to d. Note that the remaining dimensions are the same as those described with reference to FIG. 15A, and the width $W_0$ of the slit 23 is set to 1 mm; and the diameter D of the electrode 3, 7 mm.

In this case, the total sum L of the lengths of the contour lines of the slit 23 and the electrode 3 is $2(d-1)\pi + 2d\pi + 7\pi$. Also, the total area S of the electrode 3 is $3.5^2\pi - d^2\pi + (d-1)^2\pi$.

When L and S are substituted into Equation (13), Equation (14) is obtained.

[Equation 14]

$$\frac{2(d-1)\pi + 2d\pi + 7\pi}{3.5^2\pi - d^2\pi + (d-1)^2\pi} = m \times 0.57 \quad (14)$$

When Equation (14) is solved with respect to d, Equation (15) is obtained.

[Equation 15]

$$d = \frac{7.5525m - 5}{1.14m + 4} \quad (15)$$

Figure 17:
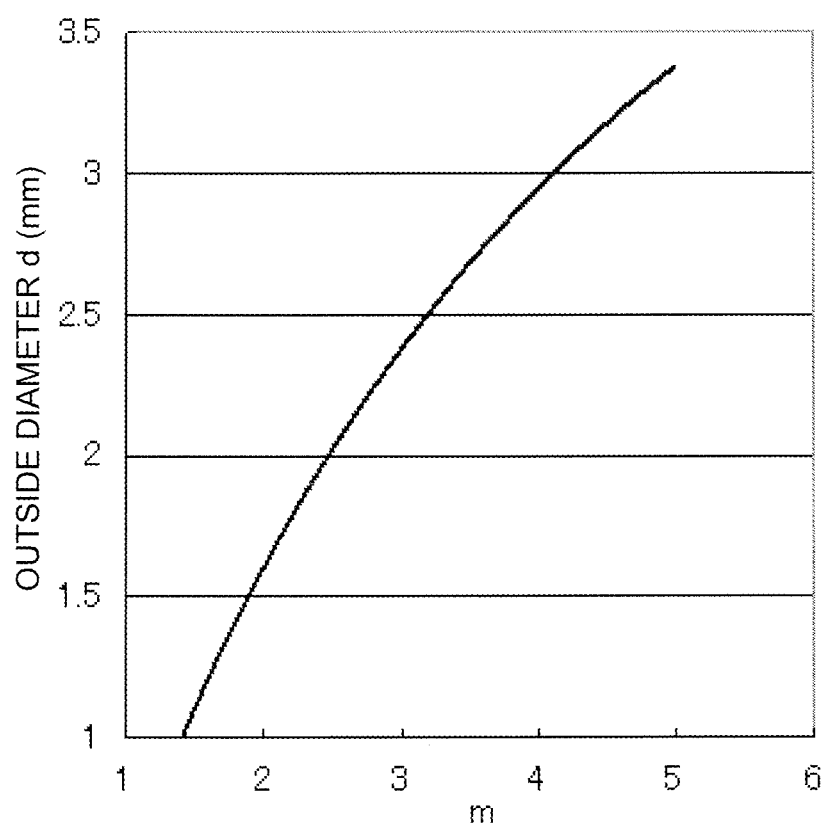
FIG. 17 is a graph representing a relationship between m and an outside diameter d of the slit in the second example of the embodiment.

FIG. 17 is a graph representing a relationship between m and the outside diameter d in Equation (15).

The outside diameter d in order for the QCM sensor to have the sensitivity which is m times that in the absence of the slit 23 may be determined by utilizing the graph of FIG. 17 or Equation (15).

According to the second example, as described above, an increase in the sensitivity of the QCM sensor 30 may be achieved, and also, the outside diameter d of the slit 23 for obtaining a predetermined sensitivity may be simply determined from Equation (15) or the graph of FIG. 17, thus facilitating design of the QCM sensor 30.

Note that in the second example, the slits 23 are provided as the pattern for increasing the above-described ratio (L/S), but the shape of the pattern is not limited to the above, and patterns of various shapes may be adopted as given below.

Figure 18:
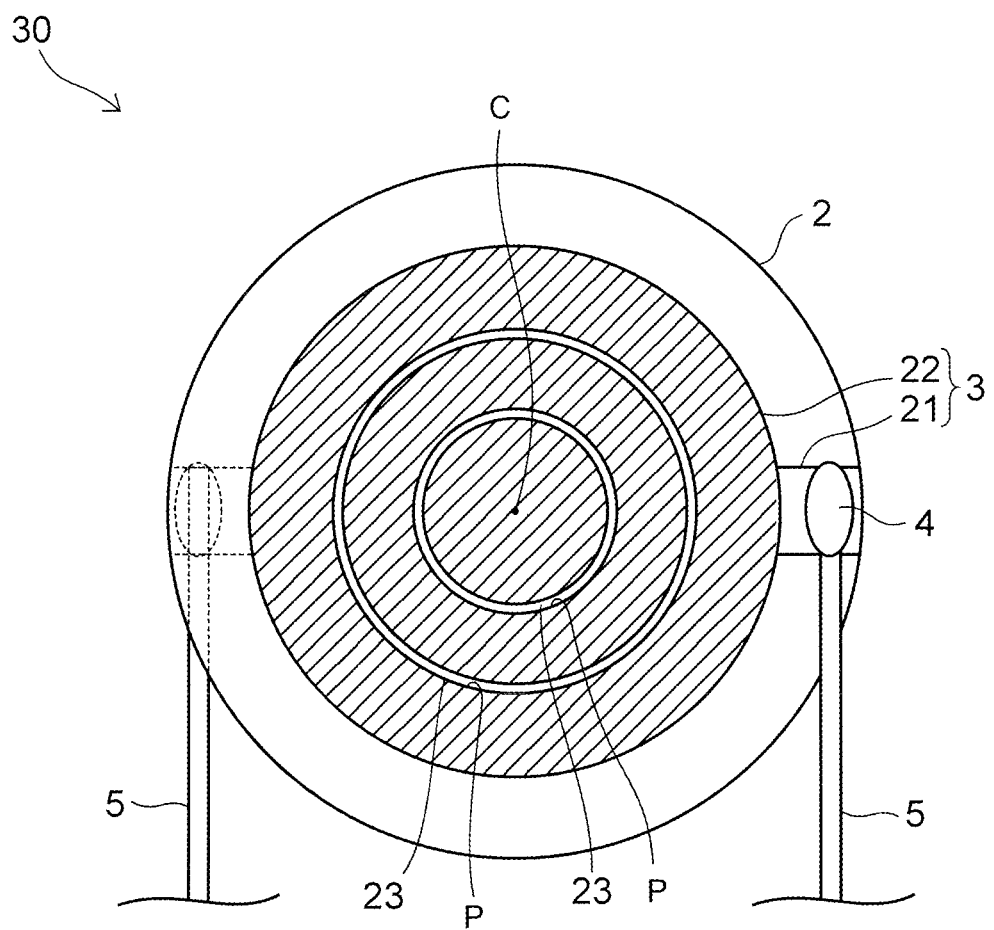
FIG. 18 is a planar view (Part 1) illustrating another example of the pattern provided on the QCM sensor according to the second example of the embodiment.
Figure 19:
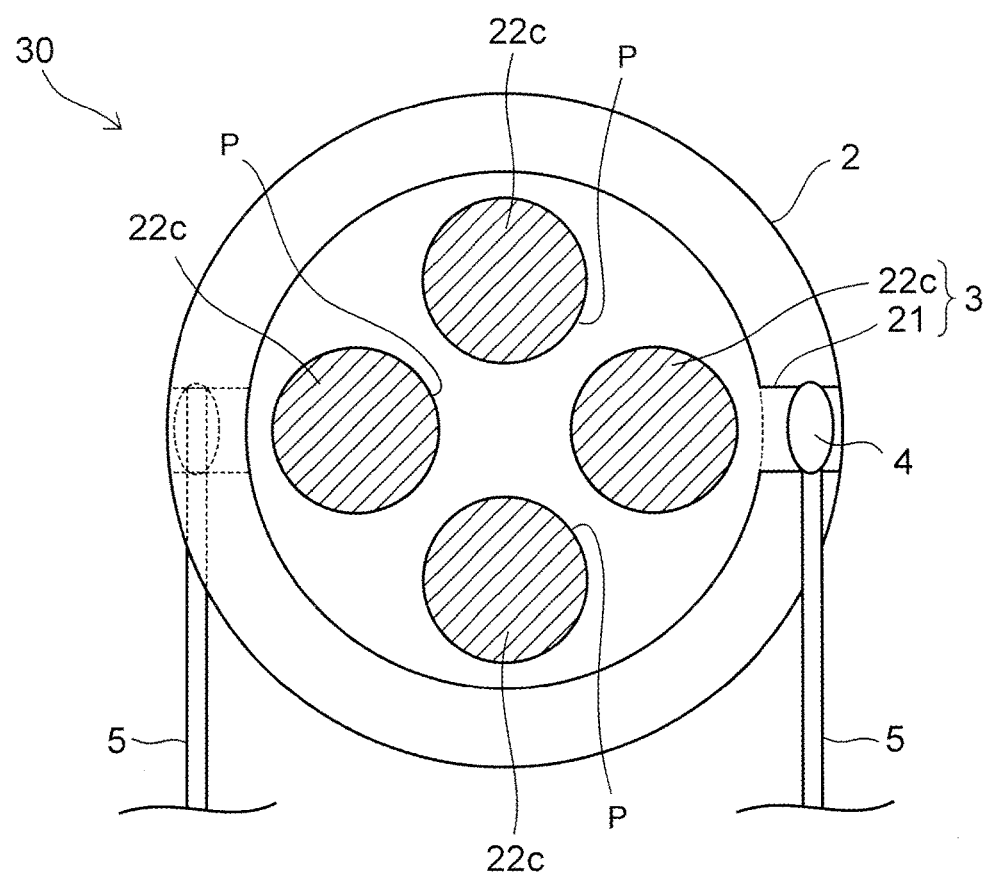
FIG. 19 is a planar view (Part 2) illustrating another example of the pattern provided on the QCM sensor according to the second example of the embodiment.

FIGS. 18 and 19 are planar views illustrating other examples of the pattern provided on the QCM sensor 30. Note that in FIGS. 18 and 19, the same structural elements as those described with reference to FIGS. 15A and 15B are designated by the same reference characters as those in these figures, and description of the same elements will be omitted hereinafter.

In the example of FIG. 18, plural annular slits 23 are concentrically provided as the pattern. Note that the slits 23 are concentric with the center C of the electrode 3.

Also, in the example of FIG. 19, plural circular isolated islands 22c are provided as the pattern of the second metal film 22.

In either of FIGS. 18 and 19, the sensitivity of the QCM sensor 30 may be increased by the contour lines P of the pattern such as the slits 23 or the islands 22c and the electrode 3.

Third Example

In the above-described first and second examples, the first metal film 21 and the second metal film 22 are stacked one on top of another to form the electrode 3.

As previously mentioned, the first metal film having the lower reactivity to the corrosive gases serves to ensure the function of the electrode 3 and oscillate the QCM sensor even after the second metal film 22 has corroded completely away.

However, in a case where the QCM sensor is not used after the second metal film 22 has corroded completely away, the first metal film 21 may be omitted so that the second metal film 22 alone forms the electrode 3, as will be described below.

Figure 20:
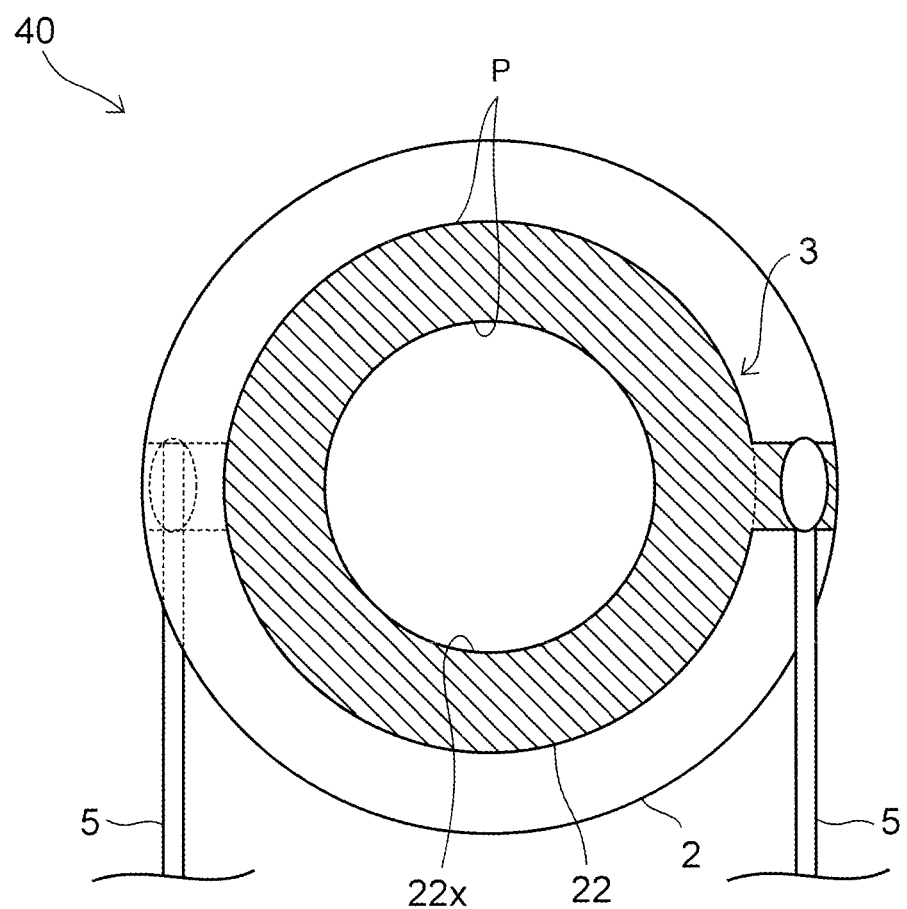
FIG. 20 is a planar view of a QCM sensor according to a third example of the embodiment.

FIG. 20 is a planar view of a QCM sensor 40 according to the third example. Note that in FIG. 20, the same structural elements as those described with reference to FIGS. 10A and 10B are designated by the same reference characters as those in these figures, and description of the same elements will be omitted hereinafter.

In the example of FIG. 20, the second metal film 22 is formed as the electrode 3 directly on the quartz plate 2. The material for the second metal film 22 is selected according to the corrosive gas as the object to be monitored, and silver or copper, for example, may be used as the material therefor.

Also, the electrode 3 is provided with an opening 22x as the pattern for increasing the ratio (L/S). The opening 22x is thus provided, and thereby, the total sum L of the lengths of the contour lines P of the electrode 3 and the opening 22x becomes greater as compared to that in the absence of the opening 22x, so that the ratio (L/S) indicating the sensitivity of the QCM sensor 40 may be increased.

Further, all portions of the electrode 3 are connected together to thus enable reducing the risk of the electrode 3 peeling wholly off from the quartz plate 2 even if the corrosion of the electrode 3 proceeds and deteriorates adhesion between the electrode 3 and the quartz plate 2.

Figure 21:
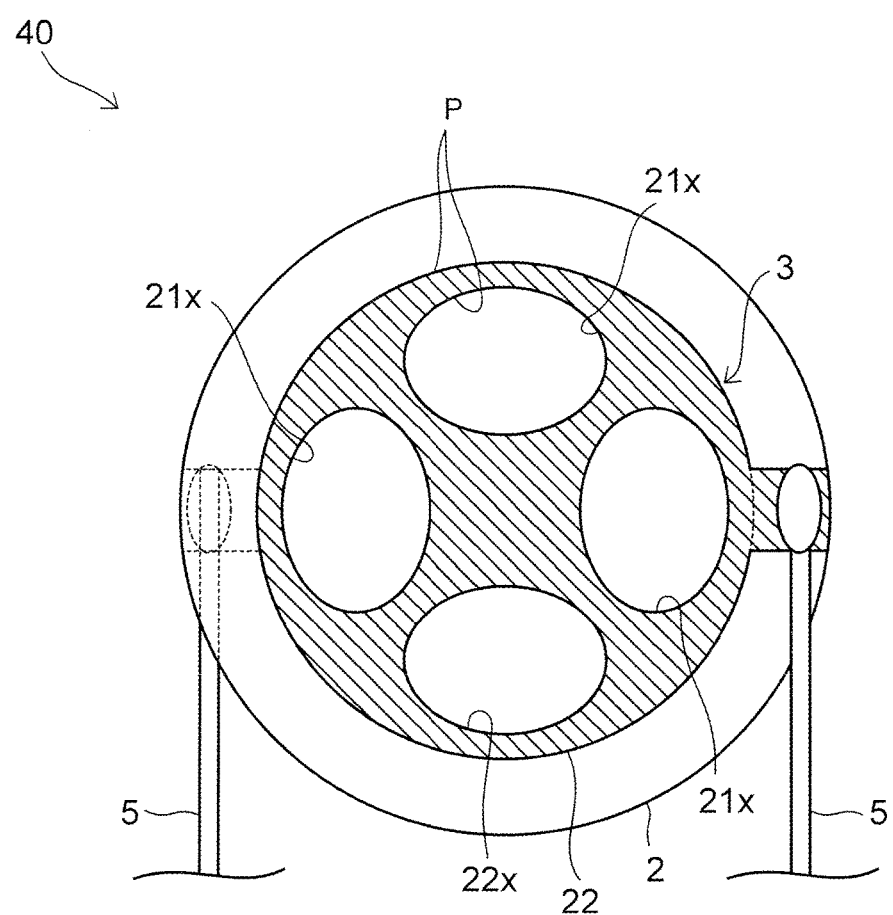
FIG. 21 is a planar view of the QCM sensor in a case where plural openings are provided in the electrode, in the third example of the embodiment.

Meanwhile, FIG. 21 is a planar view of the QCM sensor 40 according to the third example in a case where plural openings 22x are provided.

The plural openings 22x are thus provided, and thereby, the above-described total sum L of the lengths of the contour lines P becomes still greater than that in FIG. 20, so that a further increase in the sensitivity of the QCM sensor 40 may be achieved.

Also in this case, all portions of the electrode 3 are connected together to thus enable suppressing the peeling of the electrode 3 incident to the progress of the corrosion.

(Manufacturing Method) Next, description will be given with regard to a method of manufacturing the QCM sensor according to the embodiment.

Although the embodiment includes the QCM sensors according to the first to third examples as described above, description will be given below with regard to a method of manufacturing the QCM sensor according to the first example as the representative of these.

Figure 22:
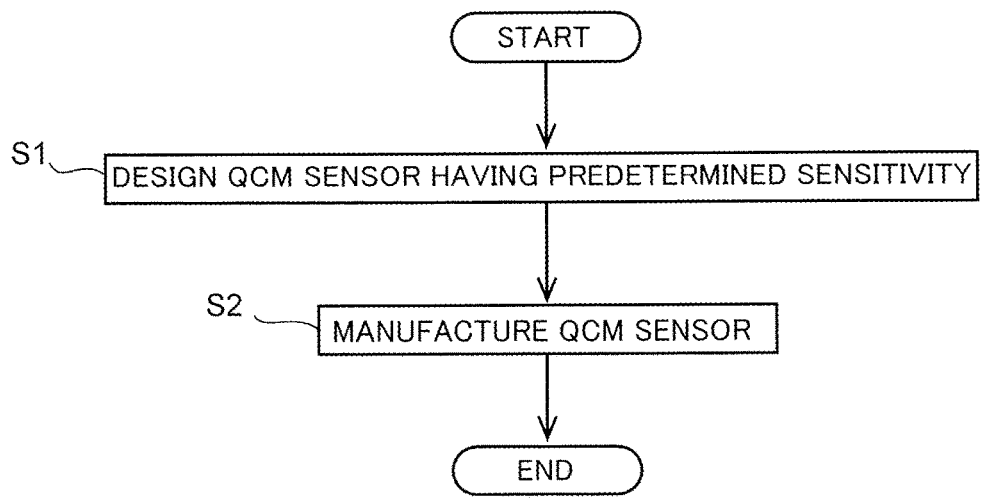
FIG. 22 is a flowchart illustrating a method of manufacturing the QCM sensor according to the embodiment.

FIG. 22 is a flowchart illustrating the method of manufacturing the QCM sensor according to the embodiment.

At first step S1 in FIG. 22, the QCM sensor having a predetermined sensitivity is designed by adjusting the total sum L of the lengths of the contour lines P and the total area S of the electrode 3.

The sensitivity is estimated from the ratio (L/S) of the total sum L to the total area S, as represented by Equation (12).

If the total sum L is set too great, corrosion in the electrode 3 proceeds rapidly and reduces the longevity of the QCM sensor, and it is therefore preferable that the total sum L be determined while keeping a balance between the longevity and the sensitivity, taking into account conditions of a measurement environment for the concentrations of the corrosive gases, or the like.

At next step S2, the QCM sensor having the total sum L and the total area S determined at step S1 is actually fabricated.

Figure 23A:
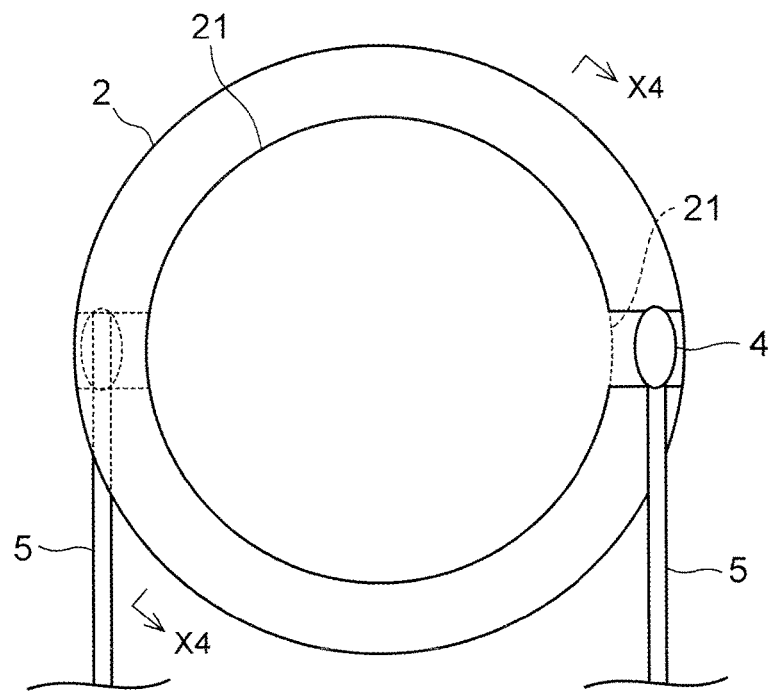
FIG. 23A is a planar view (Part 1) of the QCM sensor according to the embodiment in process of being manufactured.
Figure 23B:
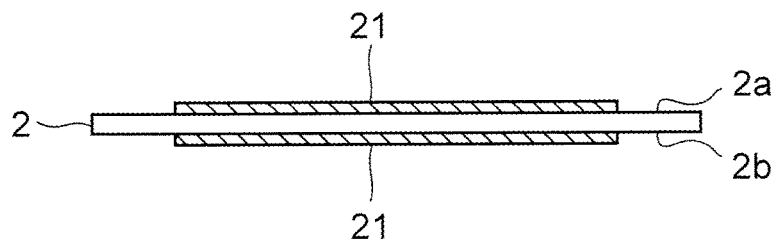
FIG. 23B is a cross-sectional view taken along line X4-X4 of FIG. 23A.
Figure 24A:
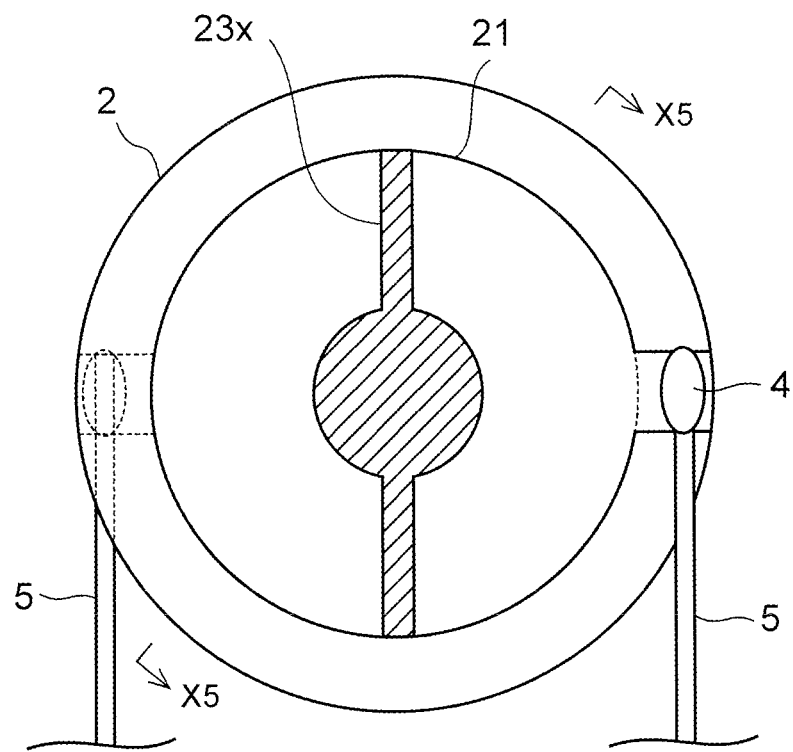
FIG. 24A is a planar view (Part 2) of the QCM sensor according to the embodiment in process of being manufactured.
Figure 24B:
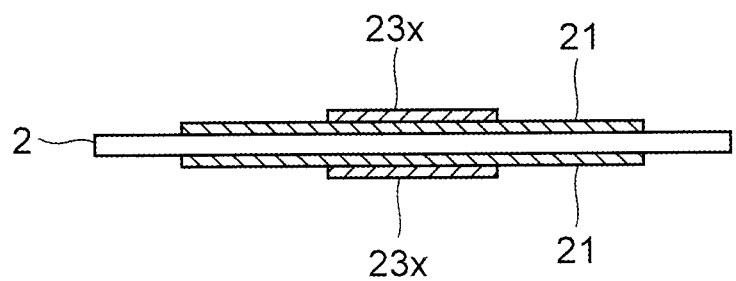
FIG. 24B is a cross-sectional view taken along line X5-X5 of FIG. 24A.
Figure 25A:
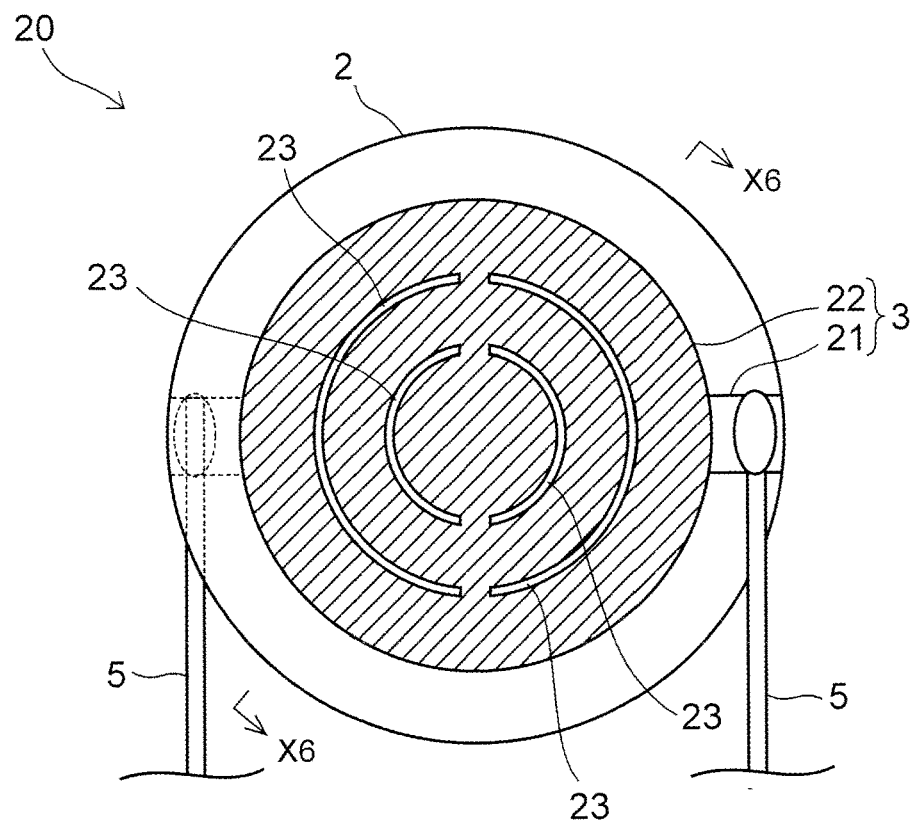
FIG. 25A is a planar view (Part 3) of the QCM sensor according to the embodiment in process of being manufactured.
Figure 25B:
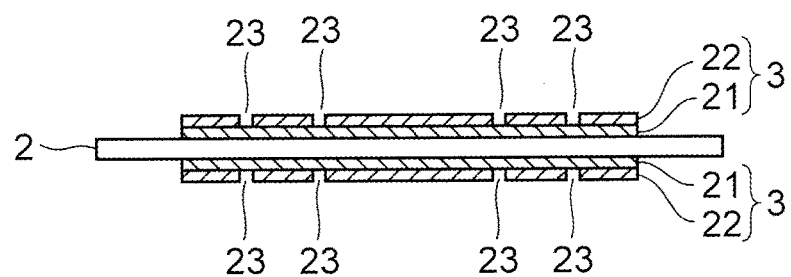
FIG. 25B is a cross-sectional view taken along line X6-X6 of FIG. 25A.

FIGS. 23A, 24A and 25A are planar views of the QCM sensor according to the embodiment in process of being manufactured, and FIGS. 23B, 24B and 25B are cross-sectional views thereof.

First, as illustrated in FIG. 23A, the first metal film 21 subjected to patterning in substantially a circular shape is formed on the quartz plate 2 by a vapor deposition process or the like.

As previously mentioned, the material having the lower reactivity to the corrosive gases may be used as the material for the first metal film 21. In this example, a gold film having a thickness of about 0.1 μm is formed as the first metal film 21.

FIG. 23B is a cross-sectional view taken along line X4-X4 of FIG. 23A.

As illustrated in FIG. 23B, the first metal film 21 is formed on each of the one and the other principal surfaces 2a, 2b of the quartz plate 2.

Then, as illustrated in FIG. 24A, a silver film or a copper film is formed on the first metal film 21 by a vapor deposition process thereby to form the connection portion 23x.

Figure 26A:
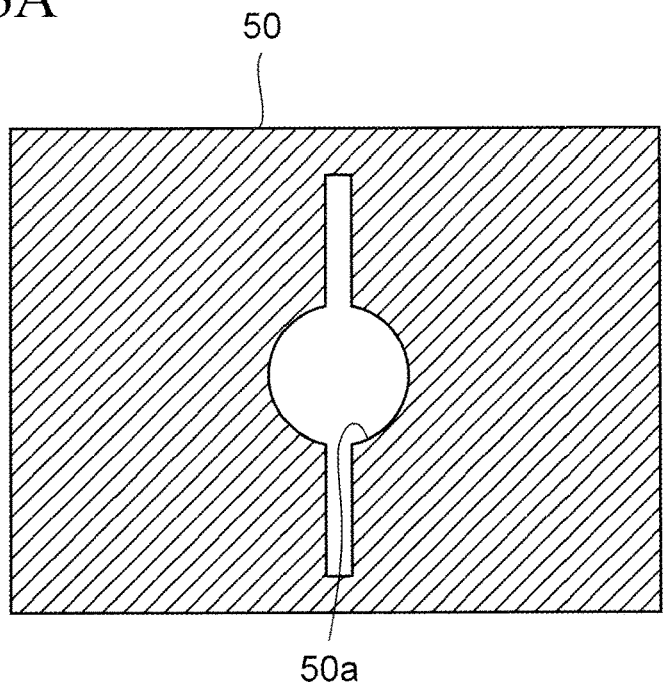
FIG. 26A is a planar view of a stencil mask for use in the process of FIG. 24A.

In the vapor deposition process, by using a stencil mask 50 illustrated in a planar view of FIG. 26A, silver atoms or copper atoms are deposited on the first metal film 21 through an opening 50a in the stencil mask 50 thereby to form the connection portion 23x shaped as illustrated in FIG. 24A.

FIG. 24B is a cross-sectional view taken along line X5-X5 of FIG. 24A.

Then, as illustrated in FIG. 25A, a silver film or a copper film is formed again on the first metal film by a vapor deposition process thereby to form the second metal film 22 having the slits 23.

Figure 26B:
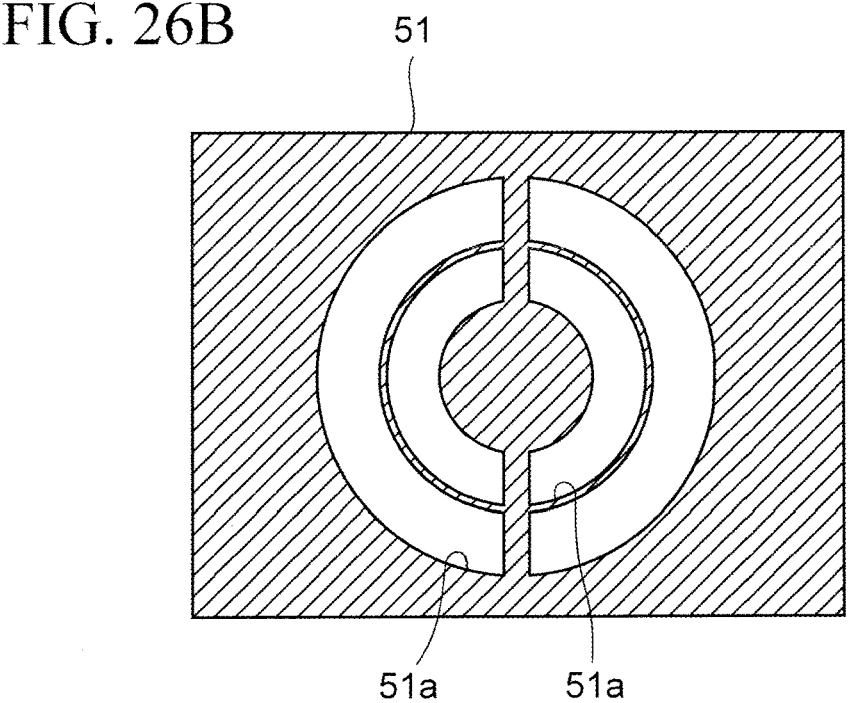
FIG. 26B is a planar view of a stencil mask for use in the process of FIG. 25A.

FIG. 26B is a planar view of a stencil mask 51 for use in this process. The stencil mask 51 is provided with an opening 51a, and silver atoms or copper atoms are deposited on the first metal film 21 through the opening 51a thereby to enable forming the second metal film 22 shaped as illustrated in FIG. 25A.

FIG. 25B is a cross-sectional view taken along line X6-X6 of FIG. 25A.

By the above, a basic structure of the QCM sensor 20 which is the same as that illustrated in FIG. 13 is completed.

Note that in the above-described example, the stencil masks 50, 51 (see FIGS. 26A and 26B) are used to subject the second metal film 22 to patterning, but FIB (Focused Ion Beam) process may be used to subject the second metal film 22 to the patterning, as will be described below.

Figure 27A:
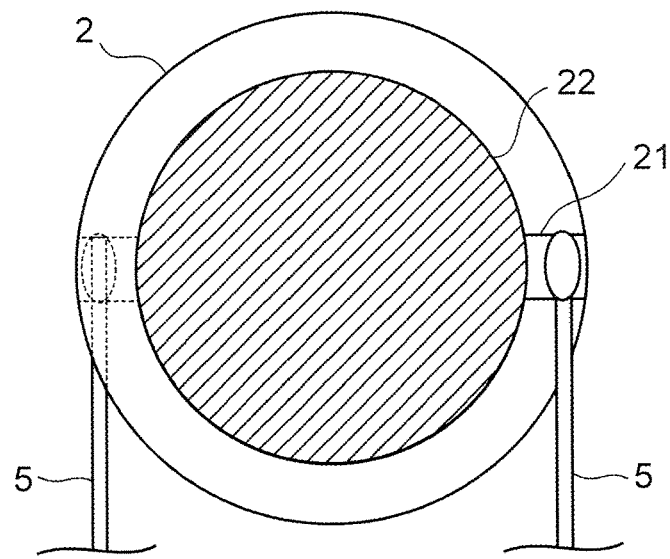
FIGS. 27A to 27C are planar views of the QCM sensor according to the embodiment in process of being manufactured, in a case where FIB process is used.
Figure 27B:
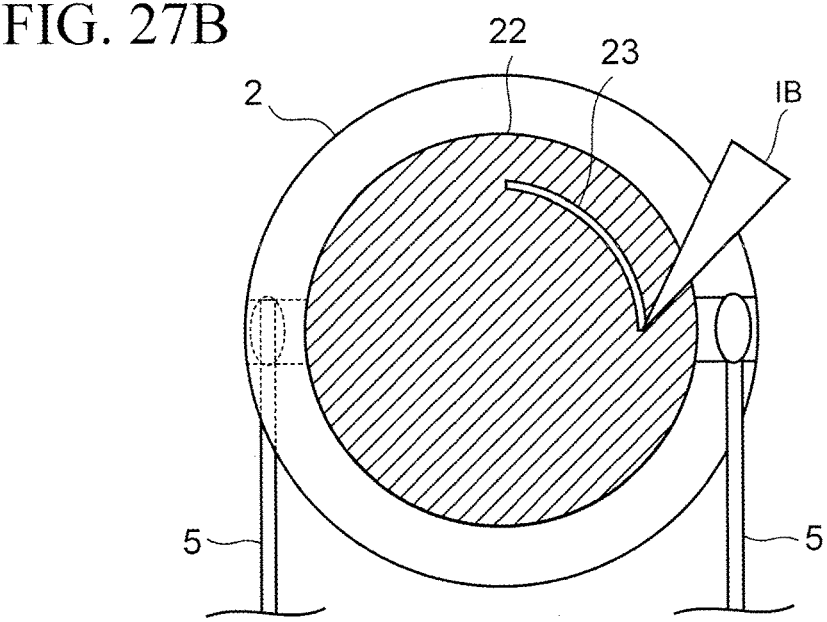
Figure 27C:
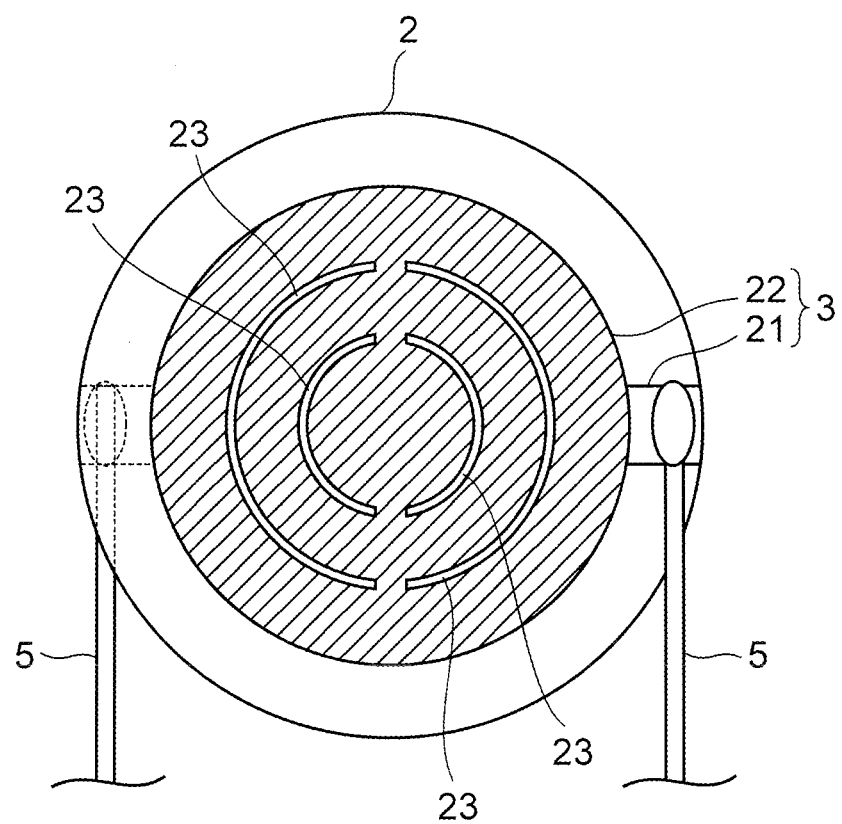

FIGS. 27A to 27C are planar views of the QCM sensor according to the embodiment in process of being manufactured, in a case where the FIB process is used.

First, as illustrated in FIG. 23A previously mentioned, the first metal film 21 is formed on the quartz plate 2, and then, as illustrated in FIG. 27A, a silver film or a copper film is formed in a thickness of about 0.1 µm as the second metal film 22 on the first metal film 21 by a vapor deposition process.

Figure 28:
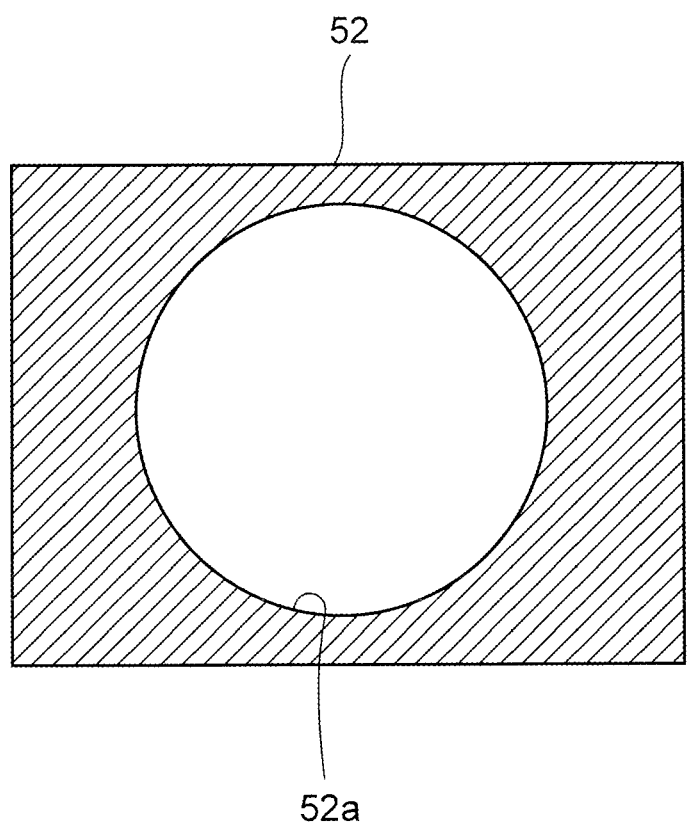
FIG. 28 is a planar view of a stencil mask for use in the process of FIG. 27A.

FIG. 28 is a planar view of a stencil mask 52 for use in this process. The stencil mask 52 is provided with a circular opening 52a, and silver atoms or copper atoms are deposited on the first metal film 21 through the opening 52a thereby to form the second metal film 22 circularly shaped as illustrated in FIG. 27A.

Then, as illustrated in FIG. 27B, the second metal film 22 is irradiated with an ion beam IB, such as a gallium ion beam, generated by an FIB process device. A portion of the second metal film 22 irradiated with the ion beam IB is evaporated, and thereby, the slit 23 is formed in the second metal film 22.

By such an FIB process, a basic structure of the QCM sensor 20 having the plural slits 23 may be obtained as illustrated in FIG. 27C.

Note that the description has been given above with regard to the method of manufacturing the QCM sensor 20 according to the first example previously mentioned, but the QCM sensor according to the second or third example may also be manufactured in the same manner as above described.

For example, the QCM sensor 30 according to the second example (see FIG. 15A) may be manufactured by forming the second metal film 22 without the connection portion 23x on the first metal film 21 by a vapor deposition process using a stencil mask in the same manner as the processes of FIGS. 24A and 24B to FIGS. 25A and 25B.

Also, the QCM sensor 40 according to the third example (see FIG. 20) may be manufactured by forming the second metal film 22 directly on the quartz plate 2 by the processes of FIGS. 24A and 24B to FIGS. 25A and 25B, with the process of FIGS. 23A and 23B omitted.

Other Embodiments

In the above-described embodiment, the slit or the opening is formed as the pattern for increasing the ratio (L/S). The pattern is not so limited, and a groove or a recessed portion may be formed as the pattern in the electrode 3.

Figure 29A:
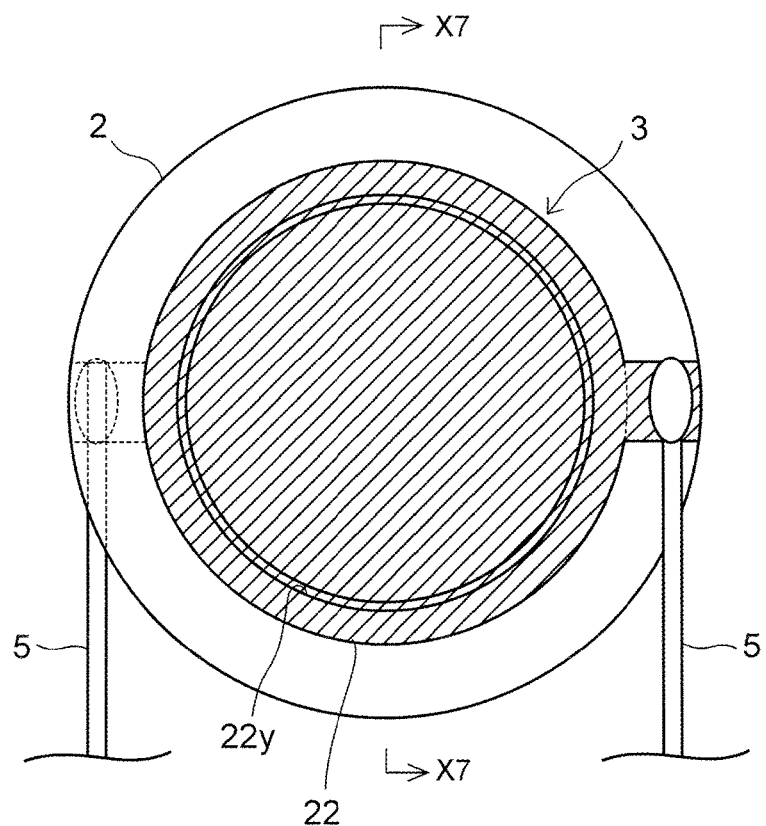
FIG. 29A is a planar view of a QCM sensor in a case where a groove is formed as the pattern in the electrode.
Figure 29B:
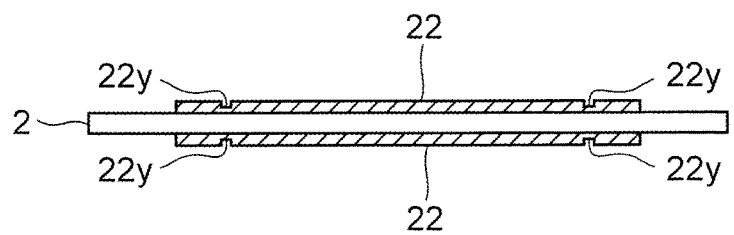
FIG. 29B is a cross-sectional view taken along line X7-X7 of FIG. 29A.

FIG. 29A is a planar view of a QCM sensor in a case where an annular groove 22y is formed as the pattern in the electrode 3, and FIG. 29B is a cross-sectional view taken along line X7-X7 of FIG. 29A.

Figure 30A:
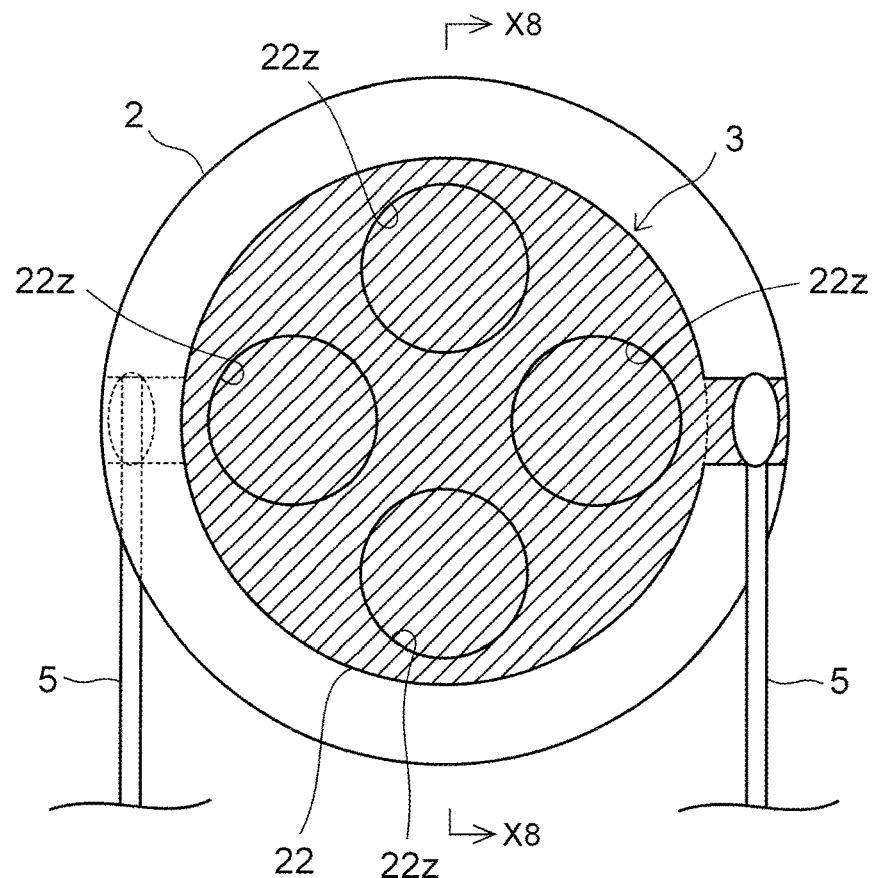
FIG. 30A is a planar view of a QCM sensor in a case where recessed portions are formed as the pattern in the electrode.
Figure 30B:
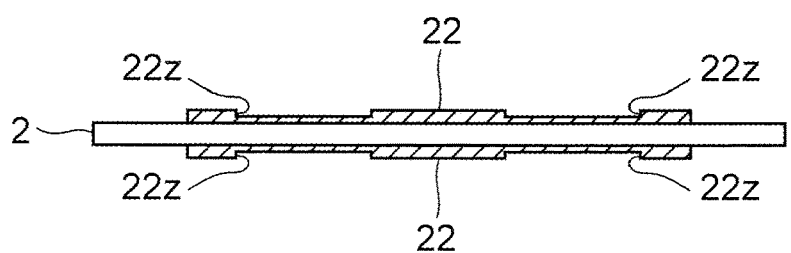
FIG. 30B is a cross-sectional view taken along line X8-X8 of FIG. 30A.

Meanwhile, FIG. 30A is a planar view of a QCM sensor in a case where recessed portions 22z each having a circular shape in the planar view are formed as the pattern in the electrode 3, and FIG. 30B is a cross-sectional view taken along line X8-X8 of FIG. 30A.

Note that in FIGS. 29A and 29B and FIGS. 30A and 30B, the same structural elements as those in FIGS. 20 and 21 described above are designated by the same reference characters as those in these figures, and description of the same elements will be omitted hereinafter.

The groove 22y or the recessed portion 22z as illustrated in FIG. 29A or 30A also has a contour line in the planar view and thus enables increasing the ratio (L/S) and hence achieving an increase in the sensitivity of the QCM sensor. Note that the groove 22y or the recessed portion 22z may be formed by etching the second metal film 22 partway along its depth.

All examples and conditional language recited herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A QCM sensor comprising:
a quartz plate having a first surface and a second surface, the first surface and the second surface being facing each other, the first surface and the second surface being both flat;
a first electrode provided on the first surface, where an entire portion of the first electrode having electrical conductivity;
a second electrode provided on the second surface, where an entire portion of the second electrode having electrical conductivity;
a first pattern formed in the first electrode, the first pattern having a first arcuate contour line in a planar view; and
a second pattern formed in the second electrode, the second pattern having a second arcuate contour line in a planar view.

2. The QCM sensor according to claim 1, wherein each of the first pattern and the second pattern is a slit.

3. The QCM sensor according to claim 2, wherein a plurality of the slits are concentrically provided.

4. The QCM sensor according to claim 2, wherein the slit formed in the first electrode has an arcuate shape concentric with a center of the first electrode, and
the slit formed in the second electrode has an arcuate shape concentric with a center of the second electrode.

5. The QCM sensor according to claim 1, wherein the pattern is a groove.

6. The QCM sensor according to claim 1, wherein all portions of the first electrode are connected in a planar view, and
all portions of the second electrode are connected in a planar view.

7. The QCM sensor according to claim 1, wherein the electrode includes a first metal film, and a second metal film formed on the first metal film and having higher reactivity to a corrosive gas than a reactivity of the first metal film.

8. The QCM sensor according to claim 1, wherein the first pattern and the second pattern have a same shape in the planar view.

9. The QCM sensor according to claim 1, wherein each of the first pattern and the second pattern has an axis of symmetry.

10. The QCM sensor according to claim 9, wherein the axis of symmetry of the first pattern is located in a plane of the first electrode, and
the axis of symmetry of the second pattern is located in a plane of the second electrode.

11. A method of manufacturing a QCM sensor, the method comprising:

forming a first electrode with a first contour line on a first surface of a quartz plate, the first surface being flat, where an entire portion of the first electrode having electrical conductivity;

forming a second electrode with a second contour line on a second surface of the quarts plate, the second surface being facing the first surface and flat, where an entire portion of the second electrode having electrical conductivity;

forming a first pattern in the first electrode, the first pattern having a first arcuate contour line in a planar view; and forming a second pattern in the second electrode, the second pattern having a second arcuate contour line in a planar view.

12. The method of manufacturing the QCM sensor according to claim 11, the method further comprising:

designing the QCM sensor having a predetermined sensitivity by adjusting a total sum of a length of the first contour line and a length of the second contour line and a total area of the first electrode and the second electrode.

13. The method of manufacturing the QCM sensor according to claim 12, wherein, in the designing of the QCM sensor, the sensitivity is estimated from a ratio of the total sum of the lengths of the first contour line and the length of the first arcuate contour line to the total area of the first electrode and a ratio of the total sum of the length of the contour line and the length of the second arcuate contour line to the total area of the second electrode.

14. The method of manufacturing the QCM sensor according to claim 11, wherein any one of a slit, and a groove is formed as the first pattern and the second pattern.

* * * * *